United States Patent [19]

Kuramoto

[11] Patent Number: 4,500,793
[45] Date of Patent: Feb. 19, 1985

[54] APPARATUS FOR MONITORING INSIDE OF TREATING COLUMN

[75] Inventor: Kenji Kuramoto, Atsugi, Japan

[73] Assignee: Ebara Corporation, Tokyo, Japan

[21] Appl. No.: 348,084

[22] Filed: Feb. 11, 1982

[51] Int. Cl.³ .............................................. G01N 15/06
[52] U.S. Cl. .................................... 250/574; 250/577; 356/414; 210/94
[58] Field of Search .............................. 209/158–161; 250/574, 577, 234, 235, 236; 356/39, 414; 73/61 R; 210/94

[56] References Cited

U.S. PATENT DOCUMENTS

| | | | |
|---|---|---|---|
| 3,388,258 | 6/1968 | Grant | 250/577 |
| 3,429,807 | 2/1969 | Burgess | 210/189 |
| 3,492,396 | 1/1970 | Dalton et al. | 356/39 |
| 3,564,266 | 2/1971 | Klotz, Jr. | 250/234 |
| 3,634,229 | 1/1972 | Stanley, Jr. | 210/675 |
| 4,123,227 | 10/1978 | Heim et al. | 250/577 |

FOREIGN PATENT DOCUMENTS

WO82/00361 7/1981 PCT Int'l Appl. ................. 356/414

*Primary Examiner*—David C. Nelms
*Assistant Examiner*—J. Brophy
*Attorney, Agent, or Firm*—Cushman, Darby & Cushman

[57] ABSTRACT

An apparatus for remotely monitoring the color distribution of two materials charged in a treating column by moving a color sensor along a viewing window of the column. The color sensor moving along the viewing window projects a light onto the materials in the treating column and receives the reflected light for conversion into a reception signal. A comparator compares the reception signal with a reference signal representing a standard color of the materials in the column to produce a digital color difference signal. The digital color difference signal is sampled and distributed to indicator lamps in accordance with position signals from the of positions sensing means which senses the passage of the color sensor by each of a plurality position. Thus, the indicator lamps provide a remote display of the color distribution of the materials along the viewing window. Further, operation processing means is provided which checks the inversion frequency of samples of the color difference signal and the inversion position or positions thereof and selectively produces one of a plurality of control signals each indicating how far the separation process has progressed.

15 Claims, 14 Drawing Figures

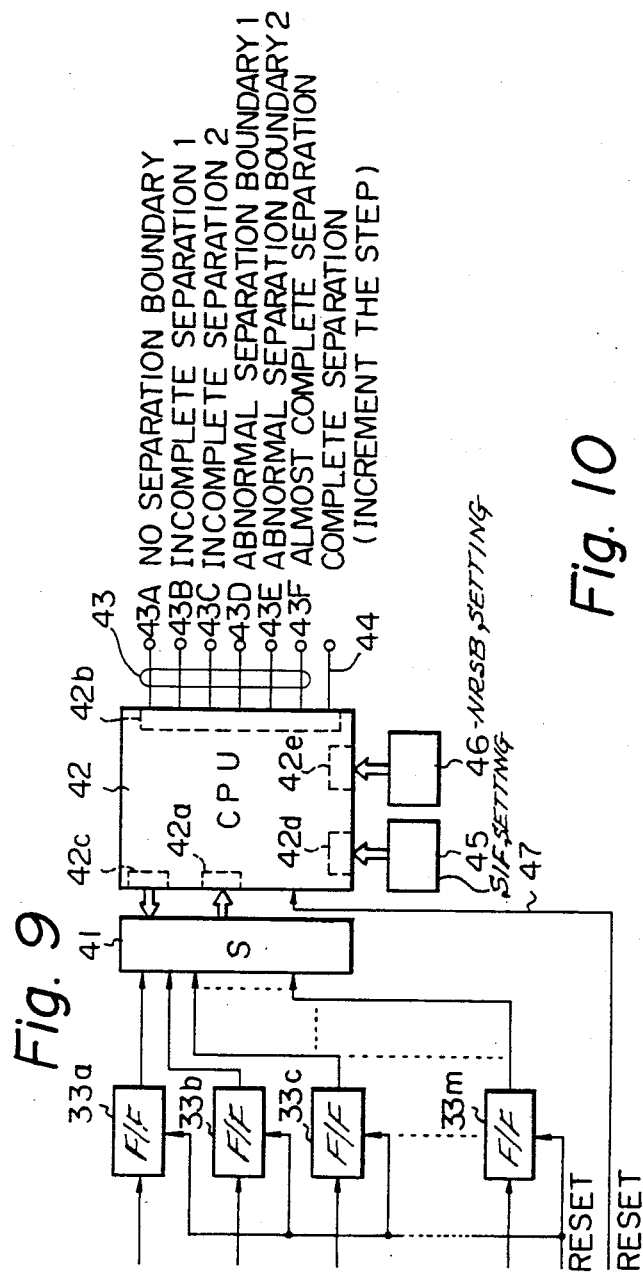

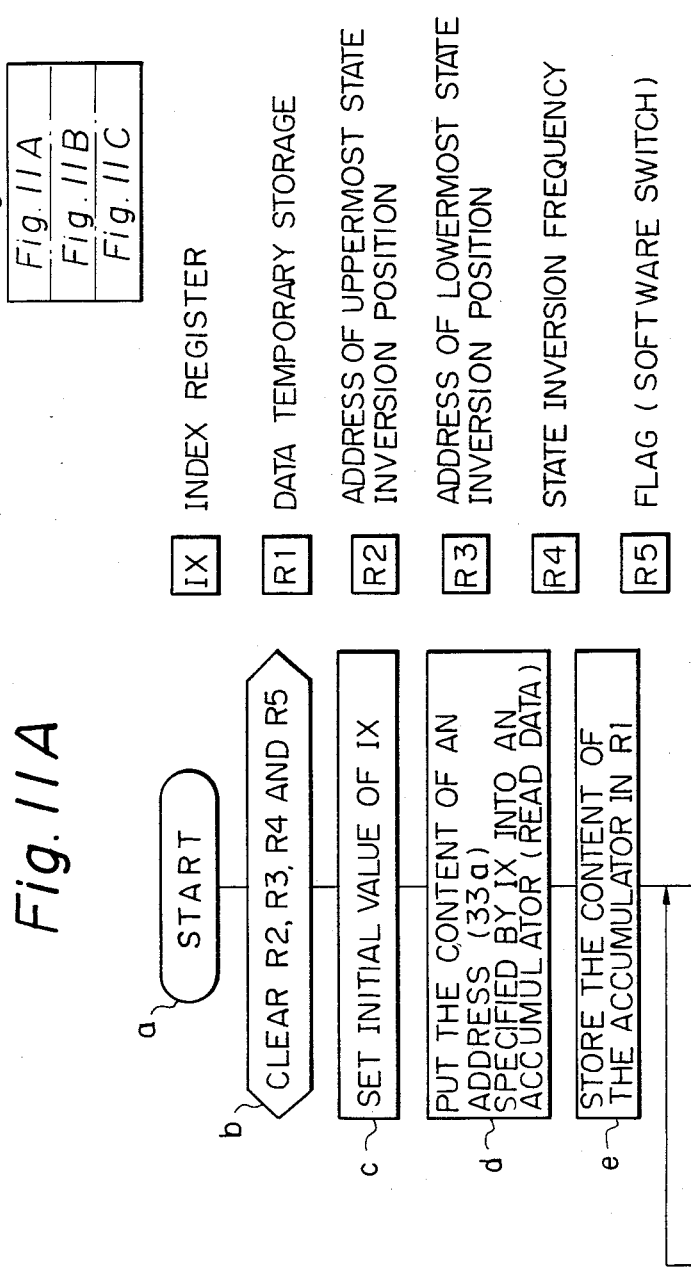

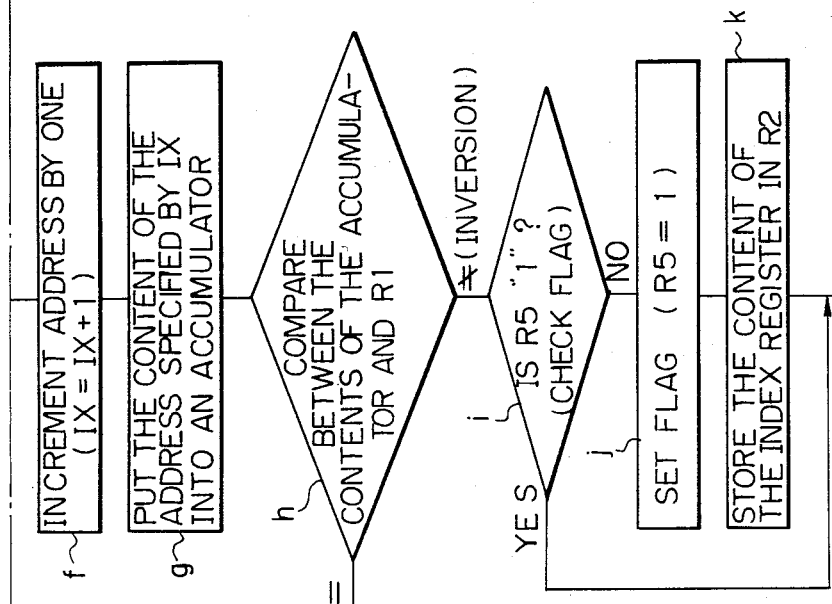

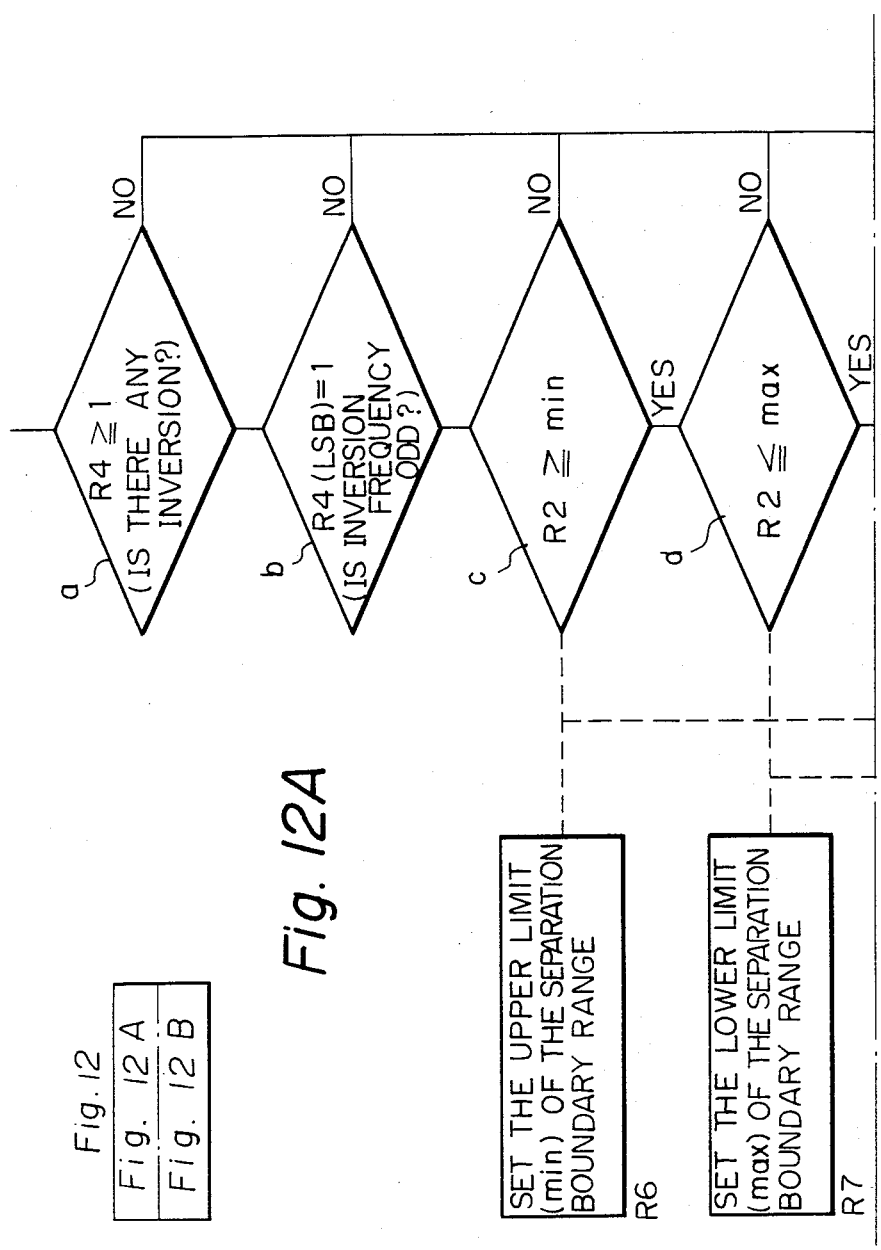

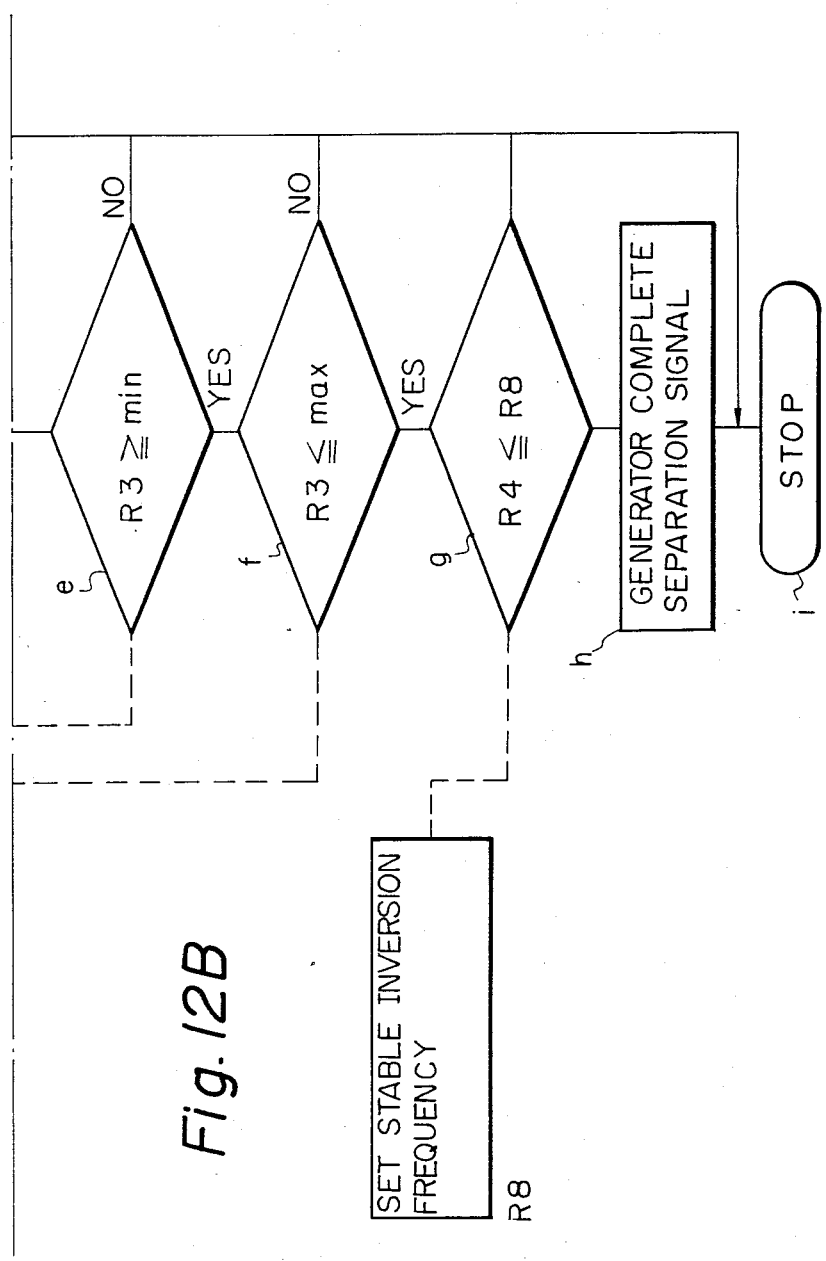

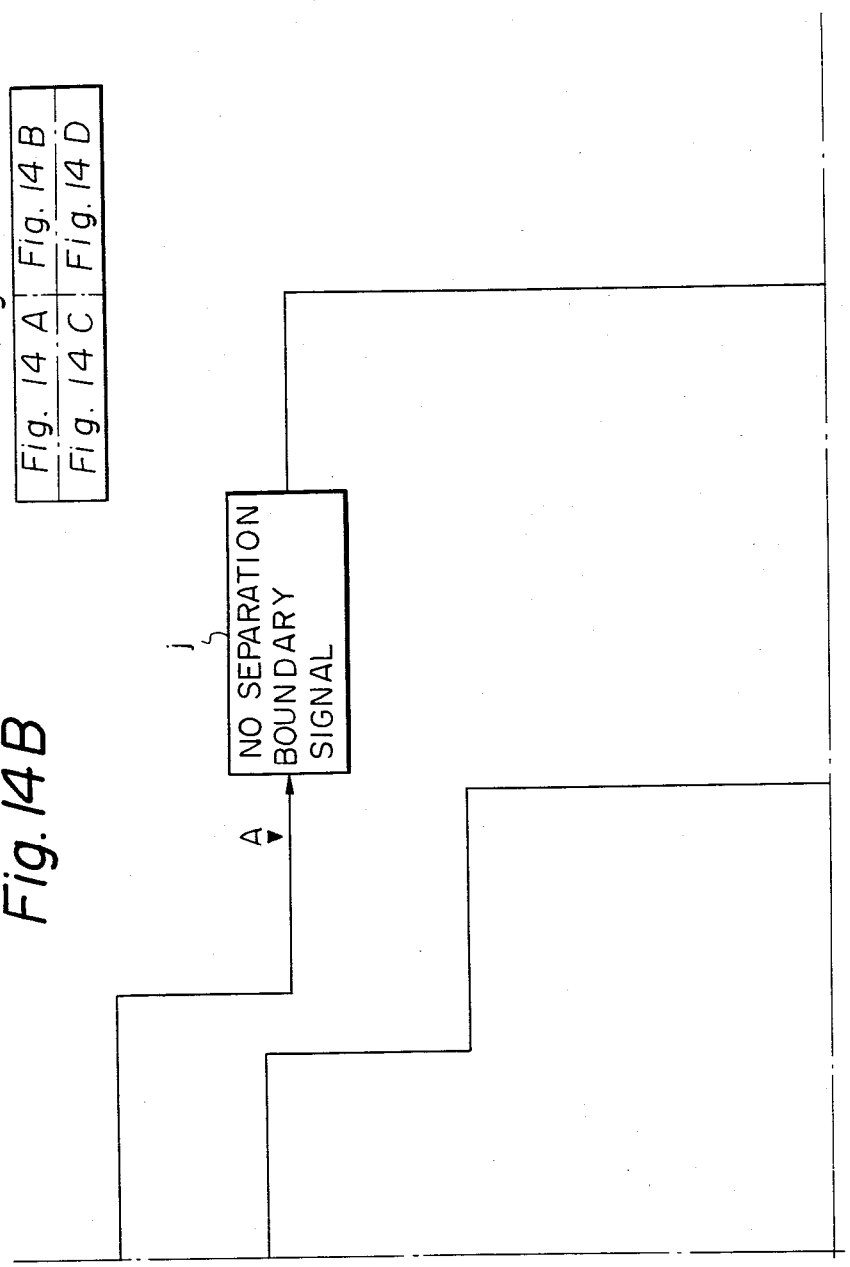

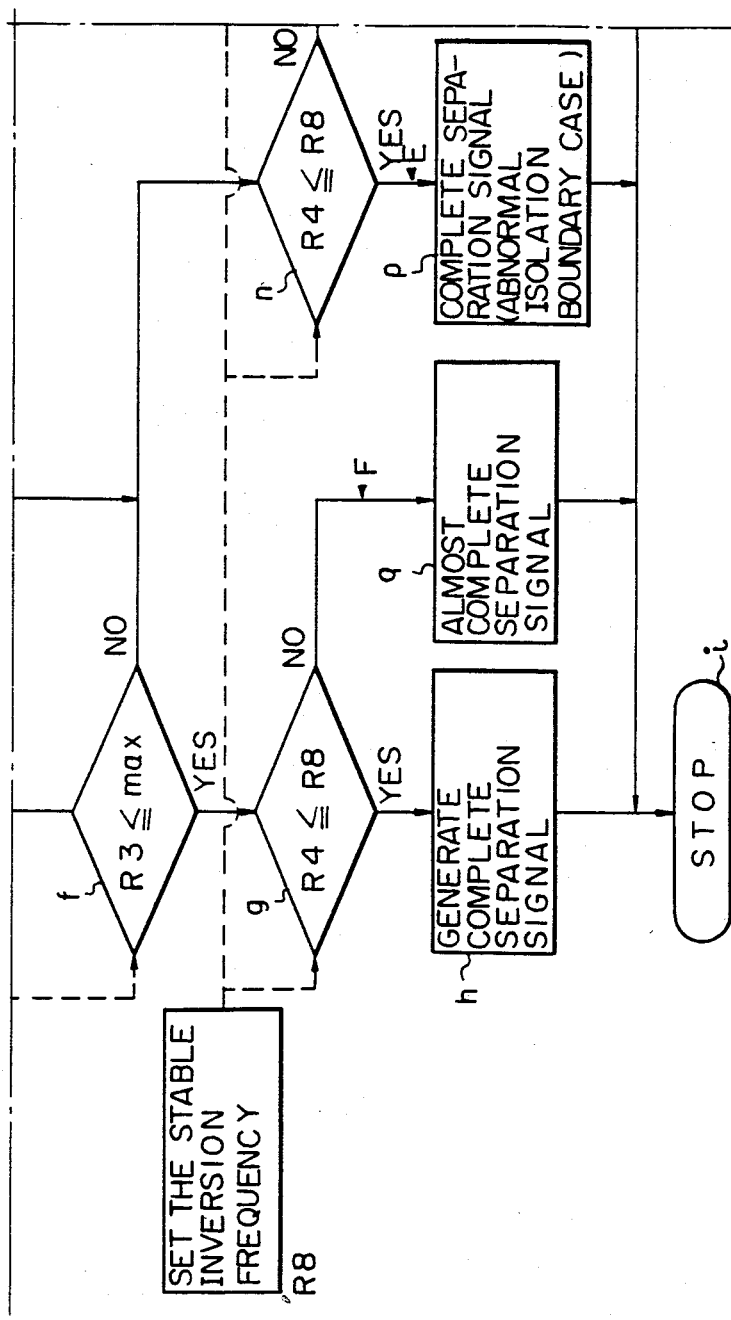

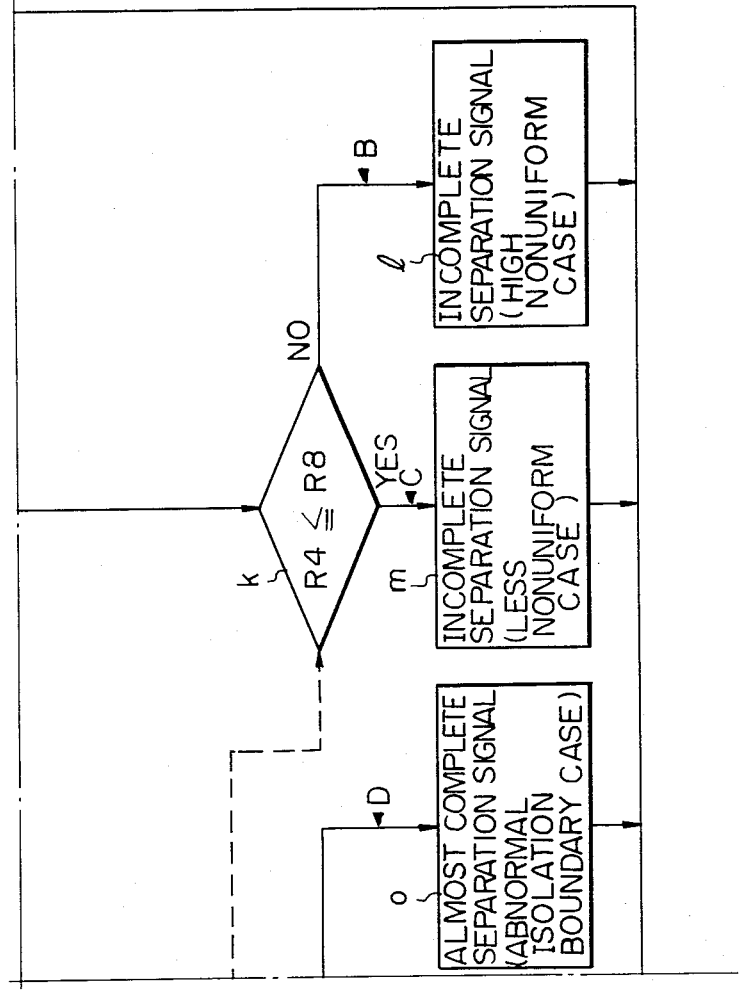

APPARATUS FOR MONITORING INSIDE OF TREATING COLUMN

FIELD OF THE INVENTION

This invention relates to an apparatus for monitoring the color change of filling materials in treating columns with change in their position therein, such as for example suitable monitors for monitoring separation of a cation exchange resin and an anion exchange resin which are different from each other in color in ion exchange resin recovering columns.

BACKGROUND OF THE INVENTION

Liquid treating apparatus for recovering pure water from polluted water using a mixture of different ion exchange resins is being widely used. In such liquid treating apparatus, as the treatment proceeds some of the cation exchange resin particles react with cations and some of the anion exchange resin particles react with anions to remove the ions from the water. However, there is a critical point where the ion exchange resin particles will be nearly saturated with cations or anions in the water after a certain period of reaction thus causing a reduction of treatment capacity and leaving most ions untreated. Such nearly ion-saturated ion exchange resins are subjected to a recovering process. Ion exchange resin saturated with different ions must be treated with different recovering agents. For example, a cation exchange resin nearly saturated with cations in the water is treated with sulfuric acid or the like while an anion exchange resin nearly saturated with anions in the water is treated with caustic soda or the like.

To prepare for the recovering process, the two kinds of ion exchange resins are separated from each other by utilizing their difference in specific gravity and their corresponding different sedimentation rates.

In a resin recovering column for the above separation process, the process must be monitored to see that normal separation is carried out. In the past, such monitoring has been done by observing a change in color. Generally, a cation exchange resin and an anion exchange resin differ in color from each other, for example dark brown for cation exchange resins and yellow brown for anion exchange resin. Such color difference has been checked visually.

More specifically, the side wall of the resin recovering column is provided with a viewing window extending longitudinally. The observer looks through the viewing window to check the difference in color of the layer structures of the anion exchange resin, which tends to form an upper layer because of its lower sedimentation rate caused by its lower specific gravity in a back washing separation process, and the cation exchange resin, which tends to form a lower layer because of its higher sedimentation rate caused by its higher specific gravity in the same back washing separation process, and the level of the boundary therebetween. From such a visual check the observer will determine how far the separation process has gone and whether proportions of the cation ion exchange resin to anion exchange resin are normal or whether the proper amount of the resin is being supplied.

An example of such prior art is provided by the patent to Burgess U.S. Pat. No. 3,429,807 and the patent to Stanley Jr. U.S. Pat. No. 3,634,229 which disclose a monitoring apparatus using a viewing glass or transparent tank through which the observer can easily check the level of the boundary between the cation exchange resin and the anion-exchange resin.

However, a visual check of the ion exchanging resin separation process is disadvantageous in that the resin separation operation must be interrupted and the observer must travel between the control panel and the recovering column to effect the visual check, thus making full automation of the recovering process impossible. It is troublesome for operators to travel between the control panel and the recovering column. Moreover, the prior art monitoring systems are not desirable from the viewpoint of safety and hygenic requirements when employed in atomic energy facilities, since operators may be harmed by irradiation from radioactive resins in the recovering column.

An attempt to automate the monitoring systems is exemplified by U.S. Pat. No. 4,120,786 to Petersen (corresponding to Japanese Patent Public Disclosure No. 56078/79) which discloses an apparatus having an elongated float responsive to the change in the density at the boundary between a cation exchange resin and an anion exchange resin. The float is suspended in a treating column charged with said two kinds of resin, and typically comprise a Westphal displacement element the top end of which is connected to a load cell. In operation, the load cell converts the displacement of the float to an electric signal which will be properly read. Thus, remote monitoring of the level of the boundary between the two kinds of resin is made possible. However, such an apparatus is not capable of continuous monitoring of the step of separation during the process while enabling a remote monitoring of the boundary level of two kinds of resin which have completely been separated. Moreover, such apparatus is not capable of determining automatically when the separation is completed. Thus, this apparatus was not suitable for fully automated separation process.

An example of apparatus for measuring the boundary level between two kinds of materials, typically a cation exchange resin and an anion exchange resin, charged in a treating column, by utilizing the color difference between the two kinds of resin is provided by Japanese Utility Model Public Disclosure No. 9533/81 (Application No. 178299/79) which discloses an apparatus having a plurality of color sensors comprising a light-projecting section and a light-receiving section each sensor of which is secured to a viewing window in alignment with each position to be sensed. In operation, respective color sensors project rays of light on the resin at the corresponding positions in the treating column. The resin reflects the lights and the color sensors receive the reflected lights. In the color sensors photoelectric transducers convert the respective reflected lights to a plurality of electric signals each corresponding to the spectrum received. The electric signals thus obtained are displayed. Thus, remote-monitoring is made possible.

However, such an apparatus is disadvantageous in that although it provides remote monitoring of the boundary level between two kinds of resin which have completely separated, a plurality of (generally a large number of) color sensors must be the same in characteristics. This makes adjustment and maintenance of the system difficult. Further, completion of separation cannot be automatically determined. Thus, this apparatus is not suitable for a fully automated separation process.

SUMMARY OF THE INVENTION

The general object of this invention is to provide an apparatus for monitoring the interior of a treating column, useful for a remote monitoring of the progress of the separation of the different kinds of materials charged therein such as ion exchange resin materials, the normality of the distribution of the materials thus separated and the gross amount of the materials being suppled. The apparatus outputs electric signals representing the color distribution of the materials along a viewing window.

The above object is achieved by the provision of an apparatus which comprises a color sensor having a light projecting portion placed to face a viewing window provided on a side wall of the treating column for projecting a light on materials in the column to be monitored through the viewing window and a light reception portion for receiving a light reflected form the materials and converting the light to a reflection signal corresponding to the color of the materials. There is provided means for driving the color sensor to move along the viewing window so that the output of the color sensor will track the color of the resins along the viewing window as the color sensor moves along the viewing window. Position sensing means is also provided which produces position signals each indicating the presence of the color sensor at one of a plurality of color detection positions spaced along the viewing window.

Another object of this invention is to provide an apparatus for monitoring the interior of a treating column which is capable of remote-displaying the level of boundary between the kinds of resin with accuracy unaffected by the color change of the resins caused by their characteristic deterioration with time.

The above object is achieved by the provision of an arrangement in which a reference color sensor which projects a ray of light on the resin at a reference position inside a treating column from its light-projecting portion and receives the light reflected from the resin by its light-receiving portion and converts the light received to a reflection signal to output a reference signal representing the color of the resin at a reference position, i.e. a reference color is provided so that a color difference signal is produced as the result of the comparison between this reference signal with a reflection signal from the color sensor moving along the viewing window. The color difference signal thus produced is sampled and distributed to a plurality of memory elements in accordance with the position signal from the position sensing means which senses the passage of the color sensor by each of a plurality of color detection positions, and the status of the color difference signal thus stored in each memory element is displayed.

An additional object of this invention is to provide an apparatus for monitoring the interior of a treating column which is capable of remote-displaying the level of the boundary between the kinds of resin with accuracy unaffected by color change of the resin caused by its characteristic deterioration with time, by means of a single color sensor without provision of the above reference color sensor.

The above object is achieved by the provision of an arrangement in which a reference position sensing means which outputs a reference position signal upon sensing passage of a color sensor of the reference position on a viewing window where the reference color of the resin is to be sensed and a reference signal storing means responsive to the reference position signal for storing as a reference signal the then existing signal from the color sensor are provided so that a color difference signal is produced as on the result of the comparison between a reference signal being supplied by the reference signal storing means and the reflection signal outputted from the color sensor moving along the viewing window.

Another object of this invention is to provide an apparatus for monitoring the interior of a treating column which is capable of remote-displaying the level of the boundary between the kinds of resin with accuracy unaffected by the color change of the resin mainly caused by its characteristic deterioration with time, by use of a reference signal generating means having an extremely simple arrangement.

The above object is achieved by the provision of an arrangement in which as a reference signal generating means a variable power source which outputs a predetermined reference signal is provided so that the color difference signal is produced as the result of the comparison between a reference signal supplied by the power source and the reflection signal. from the color sensor.

It is a further object of this invention to provide an apparatus for monitoring the inside of a treating column which eliminates visual checking of the color of the materials from a viewing window and provides full automation of the separation system by automatically and electrically judging the normality of the distribution of the materials and the completion of the separation process on the basis of the status inversion position or positions and status inversion frequency of a color difference signal sampled at a plurality of color detection positions along the viewing window and then outputting a separation completion signal to the subsequent step.

The above object is achieved by the provision of an arrangement in which an operation processing means for processing a color difference signal sampled at a plurality of color detection positions along a viewing window is provided for judging whether the separation process has been completed and outputting a control signal representing the status of the completion of the separation process to the successive step when the status inversion frequency of the color difference signal is an odd number equal to or less than a predetermined value of the stable inversion frequency and all the status inversion positions are within a predetermined normal range of the separating boundary.

Still another object of this invention is to provide an apparatus for monitoring the interior of a treating column which makes possible a precise and fully automated separation system by judging not only the completion of the separation process but also by judging the progress of the separation process and outputting a plurality of control signals representing the progress to the next step.

The above object is achieved by the provision of an arrangement in which an operation processing means for processing a color difference signal sampled at a plurality of color detection positions along a viewing window is provided for judging or recognizing the absence of the separating boundary when the status inversion frequency of the color difference signals is even, judging the abnormality of the separating boundary when the status inversion frequency is odd but at least one of the status inversion positions is out of a predetermined normal range of the separating boundary, judging the near completion of the separation process when status inversion positions are all within the predetermined normal range of the separating boundary and the status inversion frequency is odd but greater than a predetermined stable inversion number, and judging the status of the completion of the separation process when the status inversion positions are all within the normal range of the separating boundary and the status inversion frequency is odd and equal to or less than the stable inversion number, whereby one of a plurality of control signals each indicating one of the recognized states is selectively produced in accordance with the condition of materials in the treating column.

Having been so arranged as to attain these objects, this invention is industrially advantageous in that remote-monitoring of the progress of the separation process as well as the level of the separating boundary of two materials being subjected to a separation treatment in a treating column is made possible, thereby releasing operators from troublesome trips between the control panel and the treating column. This invention is advantageous also in that even when the treating column is used in atomic energy facilities, there is no danger of radioactive irradiation because operators do not need to approach the treating column. Moreover, this invention is advantageous in that full automation of the treating system is made possible by automatically or recognizing the level of the separating boundary (the normality of the distribution of two materials) and the progress of the separation process including the status of the completion of the separation process, so that visual checking can be eliminated, thereby releasing operators from unhealthy and undesirable labor.

Other objects, features and advantages of this invention will become more apparent in the following description.

BRIEF DESCRIPTION OF THE DRAWINGS

FIG. 9 is a partial block diagram of the arrangement of an operating processing means in yet another embodiment of this invention;

FIG. 10 is a view illustrating the status inversion frequency and the status inversion position of color difference signal stored in the memories shown in FIG. 9;

FIG. 12 (including FIGS. 12A and 12B) is a partial flow chart following the flow chart of FIG. 11;

DETAILED DESCRIPTION OF THE PREFERRED EMBODIMENTS

Figure 1:
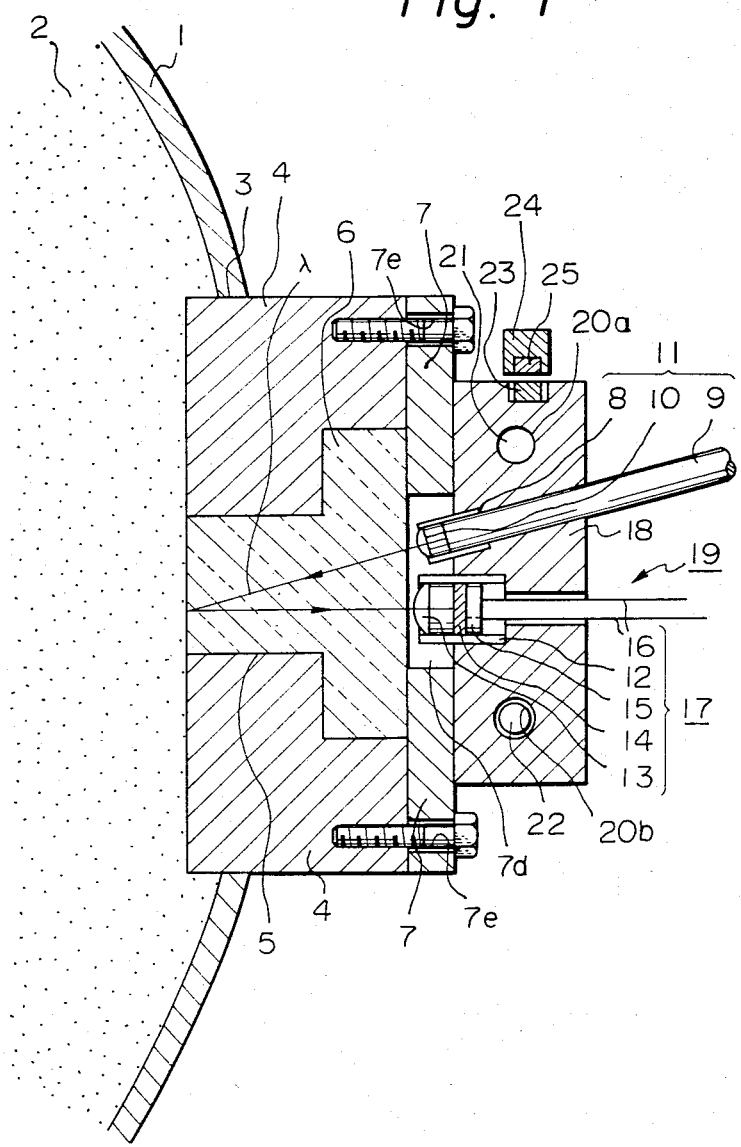
FIG. 1 is a partial diagrammatic sectional view of the construction of a treating column provided with a color sensor which is a preferred embodiment of this invention.

The embodiments of this invention are further illustrated by the following description with reference to FIGS. 1 through 14. Referring to FIG. 1, a side wall of the resin recovering column is designated by 1. The resin recovering column is charged with two kinds of resin and water. The side wall 1 is provided with an opening 3 extending longitudinally thereon. A viewing widow frame 4 is mounted in the opening 3. The viewing window frame 4 is provided with an opening 5 extending longitudinally along the central part thereof and communicating with the inside of the resin recovering column. A transparent body 6 made of acryl, heat-resistant glass or the like is fitted in the opening 5 of the window frame 4 and retained in the window frame 4 by a keep plate 7. A light-projecting section outer sleeve designated 8 incorporates an optical fiber 9 and a light-projecting lens 10 therein. Thus, a light-projecting section 11 is formed with the three members 8, 9 and 10. On the other hand, a light-receiving section outer sleeve designated 12 incorporates a light-receiving lens 13, a visibility filter 14, a photoelectric transducer 15 and light-receiving signal wires 16 therein. Thus, a light-receiving section 17 is formed with the five members 12, 13, 14, 15 and 16. The light-projecting section 11 and the light-receiving section 17 are retained rearwardly of the transparent body 6 by a supporting member 18 which is slidably mounted on the rear face of the keep plate 7 so tht a color sensor 19 is formed. The light-receiving section 17 of the color sensor is directed at an angle of 10° to 45° relative to the axis of the light-projecting section 11 so that the direct reflection from the light-projecting section 11 does not enter the light-receiving section 17.

Figure 2:
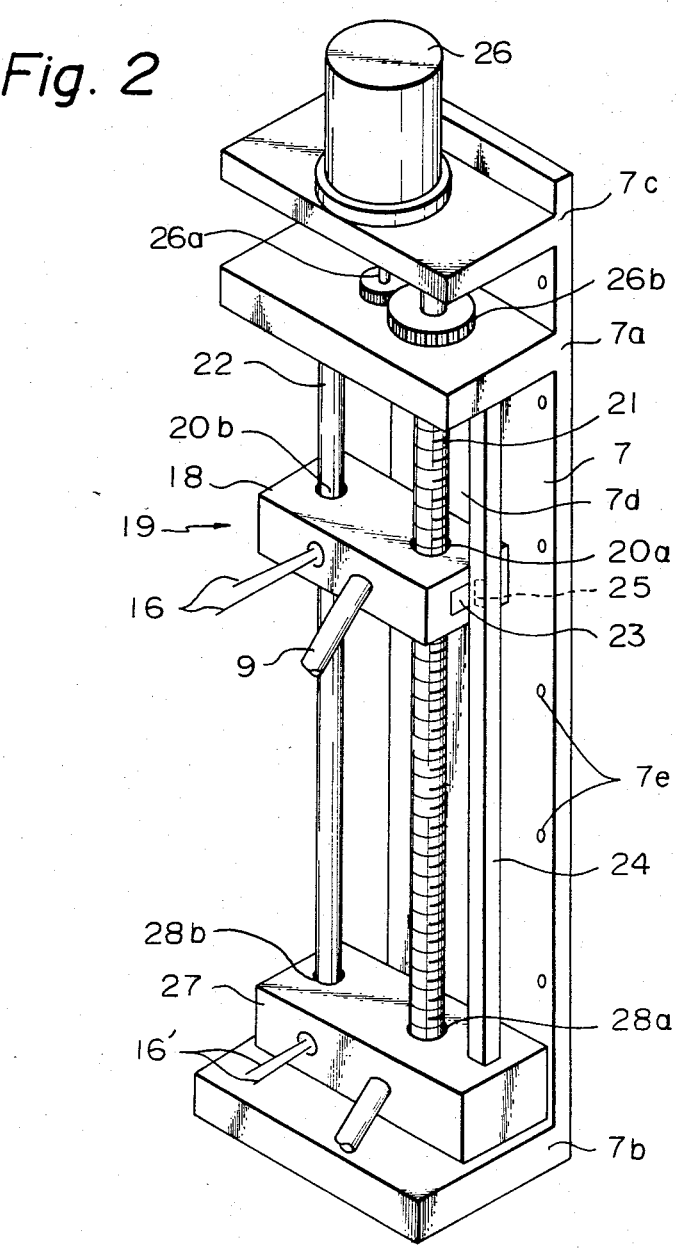
FIG. 2 is a partial perspective view of the construction of a driving means and a position sensing means for the color sensor embodying this invention.

Shown in FIG. 2 is an arrangement of a driving means and a position sensing means for the color sensor 19, One end of the supporting member 18 carrying the color sensor 19 is provided with an internally threaded hole 20a in engagement with an exteriorly threaded drive shaft 21. The upper end of the shaft 21 extends through and is rotatably supported by an upper supporting table 7a secured to the upper portion of the keep plate 7. The lower end of the shaft 21 extends through and is rotatably supported by a lower supporting table 7b secured to the lower portion of the keep plate 7.

A motor 26 is mounted on the upper side of a motor supporting table 7c secured to the top of the keep plate 7. A drive shaft 26a of the motor 26 extends through and is rotatably supported by the supporting table 7c. The drive shaft 26a is connected to the drive shaft 21 through a reduction gear 26b.

The other end of the supporting member 18 is provided with a guide hole 20b into which a guide pole 22 is slidably inserted. The upper end and the lower end of the guide pole 22 are secured to the upper supporting table 7a and the lower supporting table 7b respectively.

Moreover, mounted on one side of the supporting member 18 is a magnet 23 facing one side of a sensing pole 24 with a minute gap. The axis of the pole 24 is parallel to the surface of the magnet 23.

The side of the sensing pole 24 facing the magnet 23 is provided with a plurality of reed switches properly spaced longitudinally thereon.

As is well known to those skilled in the art, the reed switch has an arrangement in which a pair of metal pieces of a high magnetic permeability each provided with a contact point on the tip thereof are encapsulated together with an inert gas in a glass tube so that the contacts are closed in response to magnetism.

Shown at 7d is an opening provided longitudinally on the central part of the keep plate 7. The light-projecting section outer sleeve 8 and the light-receiving section outer sleeve 12 extend through the opening 7d. Shown at 7e is a bolt hole for fastening the keep plate 7 to the viewing window frame 4.

A reference color sensor 27 is fixedly placed on the lower supporting table 7b so that it faces the lowermost portion of the opening 7d. The internal construction of the reference color sensor 27 is the same to that of the color sensor 19. Shown at 28a and 28b are loose holes through which the drive shaft 21 and the guide pole 22 respectively extend.

Referring to the operation of the foregoing arrangement, a light λ from a light source not shown is emitted from the tip of the optical fiber 9, is converged in passing through the light-projecting lens 10, passes through the transparent body 6 and reaches the resin 2. The light reflects from the resin 2 with a spectral reflectivity inherent to the color of the resin, passes through the transparent body 6, converges in passing through the light-receiving lens 13, passes through the visibility filter 14 and reaches the photoelectric transducer 15 where it is converted to an electric signal and then is delivered to a display section through the reflection signal wires 16.

Figure 3A:
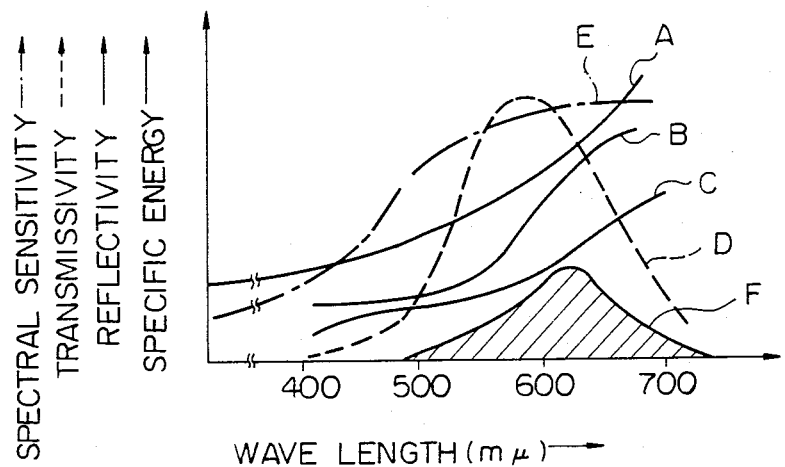
FIG. 3 is a graph showing the optical properties of the color sensor of FIG. 1.
Figure 3B:
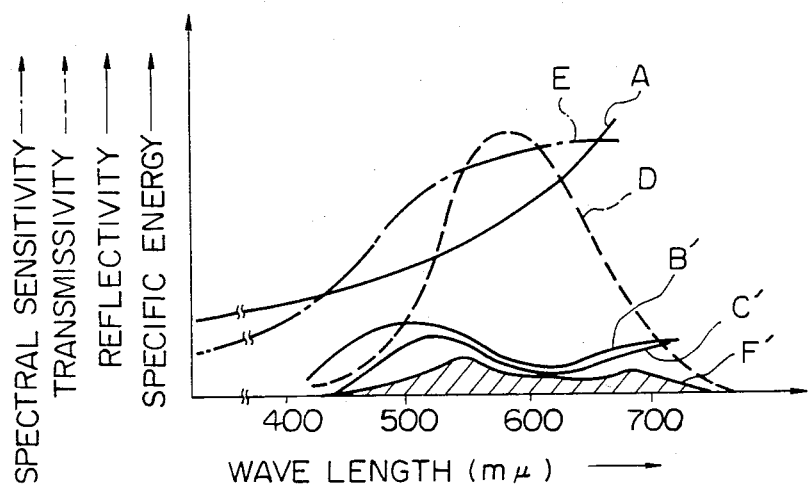

The characteristic curves of the transmissivity and reflectivity at various points in the light path are shown in FIGS. 3(A) and 3(B).

Referring to FIG. 3(A), Curve A shows a light source specific energy v.s. wave length characteristic and Curve B shows a spectral reflectivity v.s. wave length characteristic inherent in the color of the resin to be monitored. Curve C shows a reflected light specific energy, which is the product of the multiplication of the light source energy A by the spectral reflectivity B. Curve D shows the transmissivity of a visibility filter which may imitate the sensitivity of the naked eye. Curve F shows the product of the reflected light specific energy C, the transmissivity D and the sensitivity E of the photoelectric transducer of the color sensor.

Accordingly, a reflection signal having a magnitude corresponding to the area of the hatched section which is obtained by the integration of Curve F appears on the reflection signal wires 16.

FIG. 3(B) shows the characteristic curves of another resin having a different color from that of the resin of FIG. 3(B) in which Curves B', C' and F' correspond to Curves B, C and F respectively in FIG. 3(A).

In this arrangement, while the color sensor 19 is moving along the transparent body 6 of the viewing window in the side wall 1 of the resin recovering column, it produces a reflection signal indicating the color distribution of resin materials along the length of the viewing window and supplies it to the wires 16. In other words, color information indicating the color of resin materials at any position along the viewing window is obtained from the color sensor 19.

On the other hand, the reference color sensor has the same arrangement and operation as the color sensor 19 does. The reference color sensor 27 generates a reflection signal corresponding to the color of resin which has been separated at the beginning stage of the process in the resin recovering column. The reflection signal this provided serves as a reference signal for the reflection signal obtained by the color sensor 19.

Figure 4:
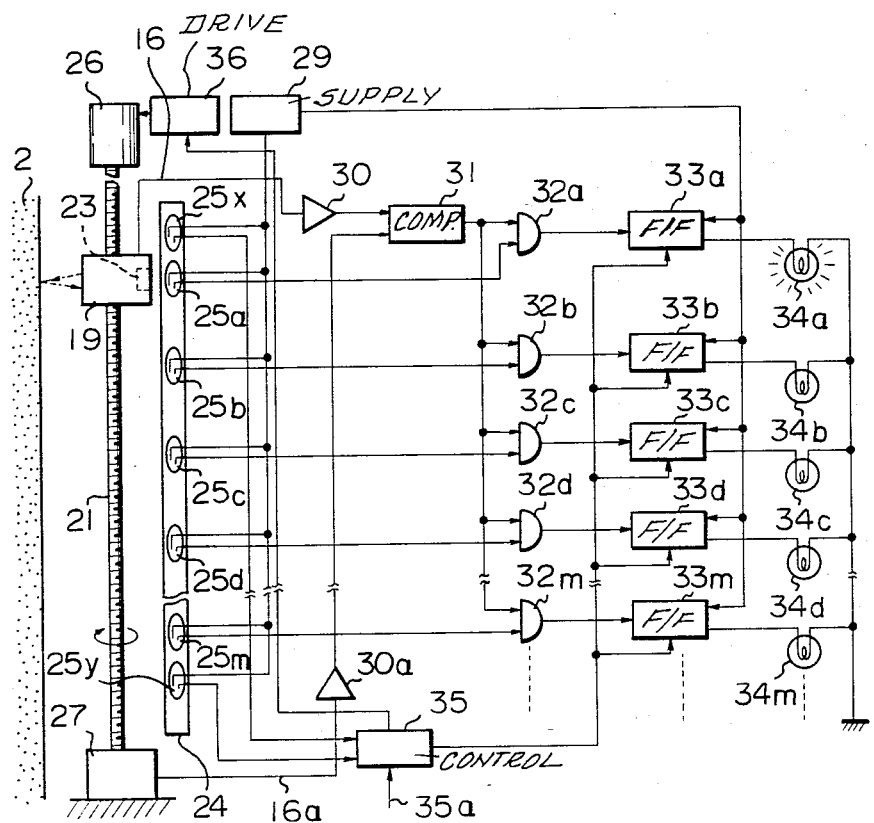
FIG. 4 is a partial block diagram of the arrangement of a color different signal displaying means embodying this invention.

FIG. 4 is a block diagram of the arrangement of a color difference displaying means following the color sensor 19 in FIGS. 1 and 2. The reflection signal line 16 is connected to one of the input terminals of a comparator 31 through a buffer amplifier 30. The other input terminal of the comparator 31 is connected to the reference signal line 16a of the reference color sensor 27 through a buffer amplifier 30a. Shown at 32a through 32m are AND gates, each of which has two input terminals, one being connected to the output terminal of the comparator 31 and the other to one of the contacts of one of the reed switches 25a through 25m. The other contact of one of the reed switches 25a through 25m is connected to a power supply 29. Shown at 33a through 33m are memories such as flip-flops and latching relays, each of which input terminal is connected to the output terminal of one of the AND gates 32a through 32m which form a distributing circuit. Each output terminal of the memories 33a through 33m is connected to one of the indicator lamps 34a through 34m. Connected to the reset terminal of each of the memories is one of the output wires of a motor control signal generating circuit 35. The power supply terminal of each of the memories is connected to the power supply 29 through a power supply line.

The sensing pole 24 is provided with an upper limit switch 25x and a lower limit switch 25y both comprising a reed switch at the upper end and the lower end thereof respectively. The limit switches are connected to the motor control signal generating circuit 35.

The other output line of the motor control signal generating circuit 35 is connected to a motor drive circuit 36.

In the above arrangement, the operation of the motor 26 rotates the drive shaft 21 which, in turn, by way of the engagement with the driving hole 20a urges the supporting member 18 downward so that the supporting member 18 carrying the magnet 23 descends slidably along the guide pole 22. While descending, the magnet 23 closes nearby reed switches in succession so that position signals each representing one of the positions of the color sensor 19 along the viewing window are successively produced.

As shown in FIG. 4, for example, when magnet 23 descends close to the reed switch 25a, the reed switch 25a closes and "1" signal is then supplied to one of the input terminals of the AND gate 32a so that the AND gate 32a is ready to provide "1" signal. A reflection signal given to the reflection signal line 16 of the color sensor 19 is supplied to the comparator 31 through the buffer amplifier 30 and compared with a reference signal which is supplied to the comparator 31 from the reference color sensor 27 through the reference signal line 16a and the buffer amplifier 30a. When the reflection signal is greater (or less) than the reference signal, the comparator 31 outputs "1" (or "0") signal as a color difference signal. This means that the color of the reflection signal is brighter (or darker) than the reference signal. When the AND gate 32a, which has been ready to provide "1" signal, receives the "1" signal from the comparator 31 through the other input terminal thereof, it outputs "1" signal to set the memory 33a in "1" state. When memory 33a changes to "1" state, the indicator lamp 34a lights up. Here, since "0" signal is supplied to one of the two input terminals of any one of the other AND gates 32b through 32m, these AND gates do not output "1" signal so that other memories 33b through 33m remain in "0" state.

As the supporting member 18 further descends, magnet 23 comes close to the reed switch 25b. When magnet 23 closes the reed switch 25b, the indicator lamp 34b lights on or keeps off, as described in the above operation, depending upon the relative luminosity of the color of the resin at the position corresponding to the position of the color sensor 19 determined by the level of the supporting member 18.

As magnet 23 moves on, reed switches 25a returns to the open state. Since the memory 33a is kep in "1" state, indicator lamp 34a remains lit.

The above operation is repeated until supporting member 18 descends close to the reed switch 25m provided at the lower end of the sensing pole 24. It is noted that the color difference signal from comparator 31 is distributed and stored into a selected one of the memories under the control of the position signal from the position sensing means in the form of switches 25a–25m. By this operation, only indicator lamps indicating the color of the resin at those positions at which the color is brighter than the reference color i.e. the color of the resin at the reference position, remain lit so that indicator lamps 34a through 34m show the longitudinal color distribution of the resin along the viewing window.

Figure 5:
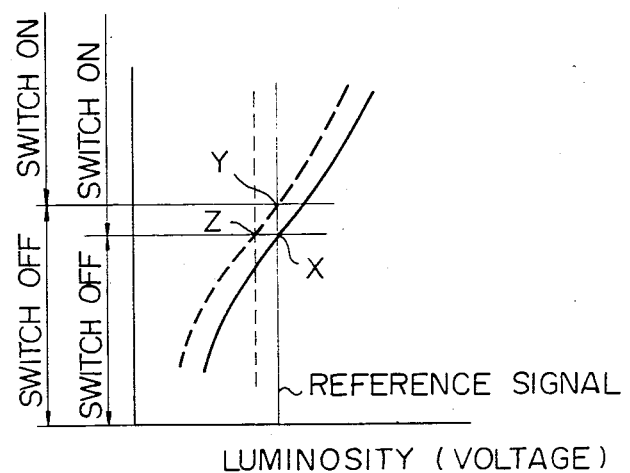
FIG. 5 is a graph showing the relationship between the brightness curve of an ion exchanging resin and the reference signal.

FIG. 5 is the brightness or luminosity curves of the resin showing the condition at which the indicator lamps light up. The indicator lamps light up for the part of the luminosity curve above the intersection X of the brightness curve and the level of the reference signal. However, it is known that as the resin materials are repeatedly used, the luminosity characteristic of the entire resin in the treating column gradually changes. The broken curve shows the luminosity characteristic of such an aged resin. Here, if the reference signal remains the same, the indicator lamps would light up for the part of the broken curve above the intersection Y rather than X. This would result in a wrong indication of the boundary between the two kinds of resin in the treating column. To resolve the above problem, this invention has an arrangement in which the reference signal generated on the basis of a part of the resin being sensed so that it changes as the color of the entire resin changes with time. With such an arrangement, the correction of the reference signal as shown by the second broken line of FIG. 5 can be automatically performed. Thus, the indicator lamps light up for the part of the broken curve above the intersection Z which represents the right boundary. As is noted from FIG. 5, the intersection Z is almost at the same horizontal level as the intersection X. Accordingly, a misindication of the boundary can be avoided.

Thus, a plurality of the indicator lamps provided corresponding to respective color detection positions along the viewing window provide a visual remote display of the separation boundary, the mixing condition and the charged level of the resin materials in the resin recovering column with a high accuracy uneffected by the color change of the resin caused by repeated use thereof.

As the supporting member 18 further descends to come close to the lower limit switch 25y provided at the lower end of the sensing pole 24, the limit switch 25y closes so that an output signal is supplied to the motor control signal generating circuit 35 which in turn causes the motor drive circuit 36 to stop the motor 26. In addition, after a desired period of time required for the operator to observe the indicator lamps, a reset pulse is supplied to the memories 33a through 33m so that the memories are reset in "0" state to turn off all the indicator lamps 34a through 34m.

When it becomes necessary to perform the monitoring operation again an actuating signal is applied to the motor control signal generating circuit 35 through an actuating signal line 35a which is energized by means of a manual switch or a timer so that the motor control signal generating circuit 35 controls the motor drive circuit 36 to start the reverse rotation of the motor 26.

Subsequently, the supporting member 18 ascends along the viewing window while performing the same operation as above. As the supporting member 18 further ascends to come-close to the upper limit with 25x, the limit switch 25x closes so that an output signal is supplied to the motor control signal generating circuit 35 to stop the motor 26 and turn off the indicator lamps 34a through 34m, thus completing the monitoring operation.

In the drawings, the reference color sensor 27 is shown to be positioned at the lower part of the viewing window. However, the reference color sensor 27 could be placed at any position wherever the color of the resin becomes stable at the initial stage of the separation process. Thus, it can be placed to face the upper part of the viewing window or a separate viewing window provided at another portion of the side wall of other resin recovering column. In such cases, it is preferred that the reference color sensor 27 may manually or otherwise be controlled in the vertical positioning independent of the color sensor 19 so that the position of the reference color sensor can be set under the charged level of resin materials which is subject to a slight fluctuation.

However, the foregoing embodiment is disadvantageous in that the incorporation of the reference color sensor 27 beside the movable color sensor 19 causes a complexity of the arrangement, raising the cost of the apparatus.

Figure 6:
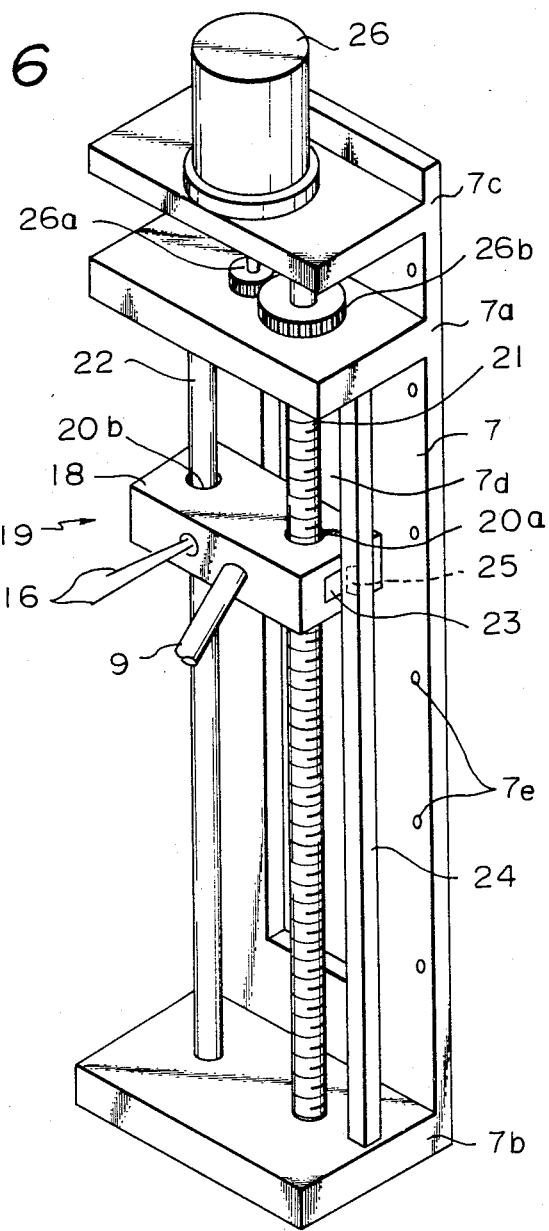
FIG. 6 is a view similar to FIG. 2 showing another embodiment of this invention.
Figure 7:
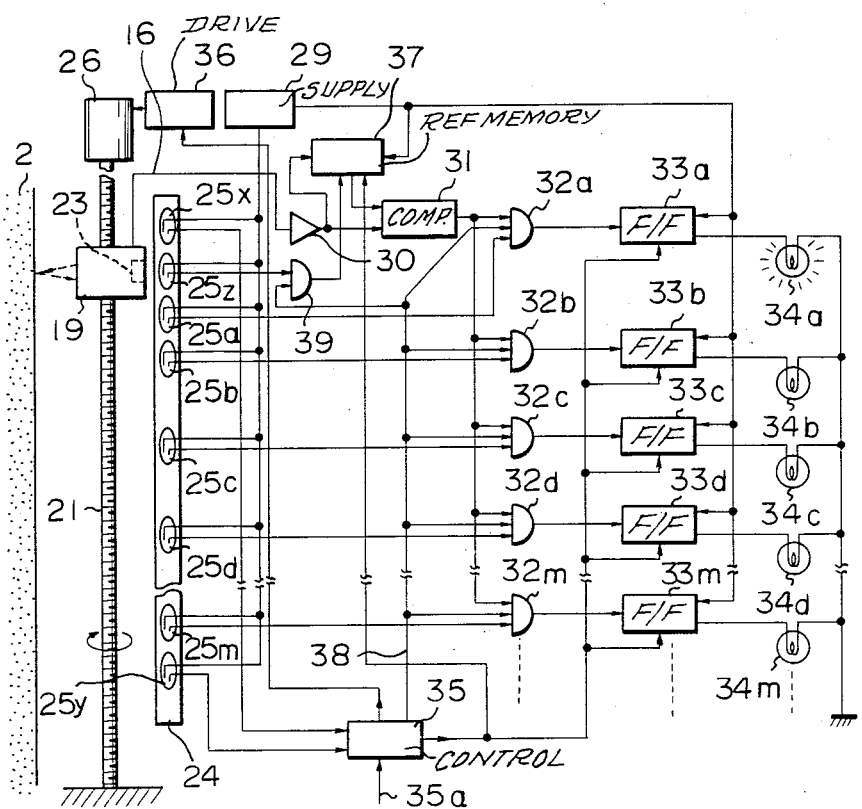
FIG. 7 is a view similar to FIG. 4 showing another embodiment of this invention.

Another embodiment of the improvement in the reference signal generating means which is adapted to use a moving color sensor 19 as a reference color sensor 27 as well to solve the above problem is illustrated by the following description with reference to FIGS. 6 and 7.

FIG. 6 is a perspective view corresponding to FIG. 2 showing the arrangement of a driving means and a position sensing means for the color sensor 19.

In the arrangement shown, no reference color sensors are placed on the lower supporting table 7b. The lower end of the drive shaft 21 extends directly into the lower supporting table 7b and is rotatably supported in a hole therein. Likewise, the lower end of the guide pole 22 extends directly into and is secured to the lower supporting table 7b.

Others members are respectively identical with those shown by the same numerals in FIG. 2.

FIG. 7 is a block diagram corresponding to FIG. 4 showing the arrangement of a color difference signal displaying means following the color sensor 19 of FIG. 6.

In the arrangement of FIG. 7, a reflection signal line 16 from the color sensor 19 which operatively moves upward and downward along the viewing window is connected to one of the two input terminals of a comparator 31 through a buffer amplifier 30 and also to the input terminal of a reference signal memory circuit 37. The memory circuit 37 includes an analog switch comprising an FET and an integrator comprising an operational amplifier. The memory circuit 37 has the function of sampling an analog voltage as an input signal upon reception of a control signal by the control terminal thereof and holds the sample until it receives a reset signal at the reset terminal.

Such a memory circuit is referred to as a sample and hold circuit and is well known to those skilled in the art.

The output terminal and the reset terminal of the memory circuit 37 are connected to the other input terminal of the comparator 31 and the output line from a motor control signal generating circuit 35 respectively. Moreover, the control terminal of the memory circuit 37 is connected to the output terminal of an AND gate 39 and one of the two input terminals of the AND gate 39 is connected to one of the contacts of a reference position sensing switch 25z.

The reference position sensing switch 25z as a reference position sensing means is a reed switch provided on the side of a sensing pole 24 at a proper position between an upper limit switch 25x and an uppermost reed switch 25a. This switch 25z is operative to sense the arrival of the color sensor 19 at the position where the reference color of the resin layer is to be sensed and output a reference position signal.

Shown at 38 is a measurement control signal line which is connected to the output terminal of the motor control signal generating circuit 35 at one end and to one of the input terminals of each of AND gates 32a through 32m at the other end. The other end of the line 38 is connected also to the other input terminal of the AND gate 39.

Other members are respectively identical with those shown by the same numerals in FIG. 4.

In the foregoing arrangement, the operation of a motor 26 rotates a drive shaft 21 so that a supporting member 18 slidably descends together with the color sensor 19 along the viewing window as in the operation described with reference to FIG. 2.

As the color sensor 19 descends and a magnet 23 secured to one side thereof comes close to the reference position sensing switch 25z, the switch 25z closes so that a reference position signal is output to supply "1" signal to one of the two input terminals of the AND gate 39. The motor control signal generating circuit 35 is supplying "1" signal to the other input terminal of the AND gate 39 through the measurement control signal line 39 so that the AND gate 39 supplies "1" signal to the control terminal of a reference signal memory circuit 37 upon reception of "1" signal from the reference position sensing switch 25z.

Since at this moment the color sensor 19 is on the reference position where the reference color of the resin layer is to be sensed, the sensor 19 generates a reflection signal corresponding to the reference color and supplies it to the input terminal of the reference signal memory circuit 37 through a reflection signal wire 16 and the buffer amplifier 30.

Thus, the reference signal memory circuit 37 receives a reflection signal corresponding to the reference color, i.e. the reference signal at its data input terminal and "1" control signal at the control terminal so that the reference signal is stored as an analog voltage in the memory circuit 37 and thereafter continuously supplied to one of the two input terminals of the comparator 31 until the memory circuit 37 receives a reset signal at its reset terminal.

Subsequently, as the color sensor 19 slides further down and the magnet 23 comes close to the reed switch 25a, the reed switch 25a closes so that "1" signal is supplied to one of the input terminals of the AND gate 32a. Since "1" signal from the motor control signal generating circuit 35 through the measurement control signal line 38 is being connected to one of the other input terminals of each of the AND gates 32a through 32m at this moment, the AND gate 32a receives "1" signals at the two input terminals so that it is enabled to output "1" signal upon reception of a signal, i.e. an output signal ("1" signal) from the comparator 31 at the remaining input terminal.

A reflection signal provided to the reflection signal line 16 of the sensor 19 is supplied to the comparator 31 through the buffer amplifier 30 where it is compared with the reference signal which is being continuously supplied thereto from the reference signal memory circuit 37.

When the reflection signal is greater (or less) than the reference signal, comparator 31 outputs "1" (or "0") signal as a color difference signal.

Thus, AND gate 32a, which has been enabled to output "1" signal, outputs "1" signal upon reception of "1" signal from the comparator 31 at the other of the input terminals to set a memory 33a in "1" state. When memory 33a changes to "1" state, an indicator lamp 34a lights up.

Here, the reflection signal is supplied also to the reference signal memory circuit 37 through the buffer amplifier 30. However, after the color sensor 19 moves away from the reed switch 25z, the latter will open and control the memory circuit 37 so that the reference signal stored in the memory is not changed by the subsequent reflection signals.

Moreover, when the color sensor 19 descends near the reed switch 25a, other AND gates 32b through 32m do not output "1" signals and memories 33b through 33m remain in "0" state since "0" signal is being supplied to one of the input terminals of each of the AND gates 32b through 32m. Thus, the color difference signal output from the comparator 31 is distributed and stored in a selected one of the memories designated by the position signal.

Subsequently, as the color sensor 19 descends further and the magnet 23 comes close to a reed switch 25b, the reed switch 25b closes so that an indicator lamp 34b lights up or remains off in response to the color of the resins at the position corresponding to the position of the color sensor determined by the level of the supporting member 18 as described above.

The above operation is repeated until color sensor 19 descends close to a reed switch 25m provided at the lower portion of the sensing pole 24. By this operation, only indicator lamps corresponding to the positions of the resins having a greater brightness than that of the reference resin can remain lit so that the indicator lamps 34a through 34m show the longitudinal color distribution of the resins along the viewing window.

As color sensor 19 descends further to come close to a lower limit switch 25y provided at the lower end of the sensing pole 24, the limit switch 25y closes to supply an output signal to the motor control signal generating circuit 35, which, in turn, controls the motor drive circuit 36 to stop the motor 26. After a desired period of time required for the operator to observe the indications of the lamps, the memories 33a through 33m are reset to put the indicator lamps 34a through 34m out. This operation is identical with that of the arrangement of FIG. 4.

However, in the arrangement of FIG. 7, the motor control signal generating circuit 35 supplies a reset pulse to the reference signal memory circuit 37 as well as to the memories 33a through 33m so that the memory circuit 37 is reset to prepare for the storage of a new reference signal.

Moreover, as the lower limit switch 27y closes, the motor control signal generating circuit 35 sends "0" signal to the measurement control signal line 38 so that the AND gates 32a through 32m and the AND gate 39 are latched to output "0" signal regardless of the signal supplied to the other input terminals thereof. Thereafter, the actuation of the motor 26 to rotate in the reverse direction moves the color sensor 19 upwardly along the viewing window.

When the sensor 19 passes by, the reed switches 25a through 25m close alternatively in reverse order. Since the AND gates 32a through 32m do not output "1" signal during this period as they did in the above descending operation, no input signals are supplied to the memories 33a through 33m.

As the color sensor 19 further ascends, the reference position sensing switch 25z closes again. Since the AND gate 39 does not output "1" signal at this moment as it did in the above descending operation, the reference signal stored in the reference signal memory circuit 37 is not renewed.

Thus, the ascending operation following the descending operation does not perform any measurement while the descending process does. Accordingly, the ascending operation is a step for returning the color sensor 19 to a level higher than the reference position to prepare for the following measuring operation.

The returning step is necessary for the comparison of the reflection signal which is given at each measuring operation with an "updated" reference signal which will be updated at the beginning of each descending operation. The newly sensed or updated reference signal is stored in the reference signal memory circuit 37 before the color sensor 19 comes close to the uppermost reed switch 25a.

As the color sensor 19 further ascends to the position of the upper limit switch 25x, the limit switch 25x closes so that the motor control signal generating circuit 35 supplies "1" signal to the AND gate 32a through 32m and the AND gate 39 through the measurement control signal line 38, whereby the AND gates 32a through 32m and the AND gate 39 are enabled to output "1" signal to prepare for the following measurement and the motor drive circuit 36 stops the motor. Thus, one monitoring cycle is completed.

As an example of the reference signal memory circuit 37, a sample and hold circuit for storing analog voltages is employed in the above embodiment. In the alternative, the memory circuit 37 may comprise analog-digital transducers and digital memories such as a RAM. In this case, the comparator 31 may comprise a digital comparison logic circuit which comparison is performed between a digital code representing the reference signal output from the reference signal memory circuit 37 and a digital code representing the reflection signal output from the color sensor 19 at each position.

Figure 8:
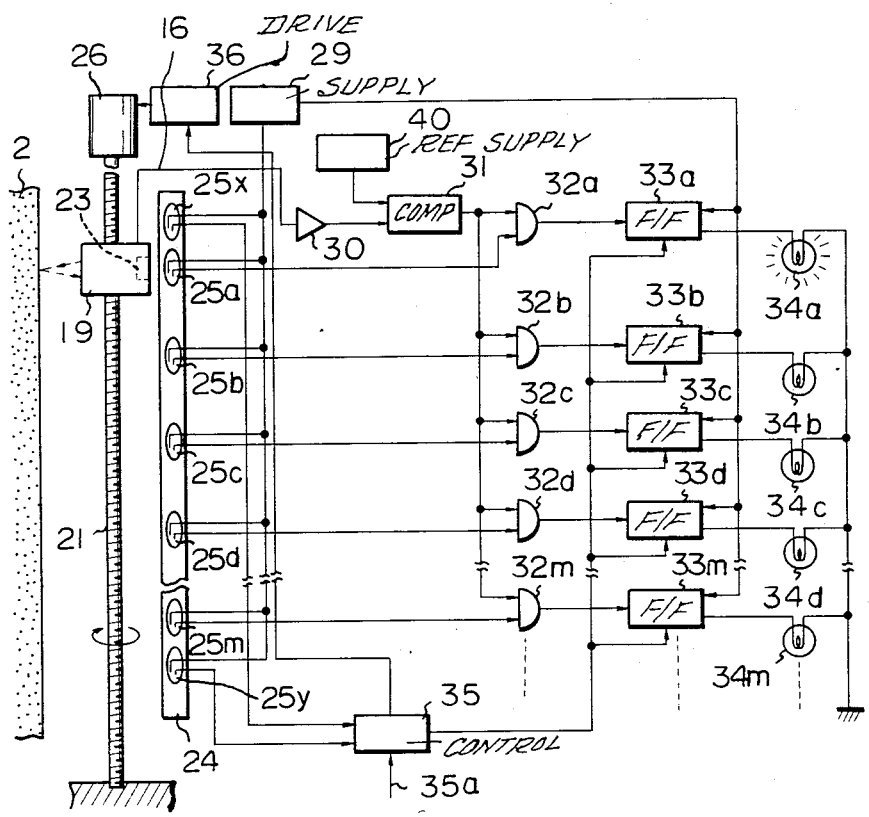
FIG. 8 is a view similar to FIG. 4 showing still another embodiment of this invention.

An alternative embodiment of the reference signal generating means of this invention, which is directed to a more simplified arrangement, is illustrated by the following description with reference to FIG. 8. The simplification of the arrangement is made by the elimination of the reference color sensor 27 as shown in FIG. 4 and the reference signal memory circuit 37 as shown in FIG. 7.

FIG. 8 is a block diagram showing the arrangement of a displaying section. Connected to one of the two input terminals of a comparator 31 is the output terminal of a reference power supply 40 as a reference signal generating means which comprises a stabilized power supply capable of setting voltages. Other elements are respectively identical with those having the same reference numerals in FIG. 4.

In the above arrangement, a specified reference signal predetermined by the operator on the basis of a supposed reference color of the resin is supplied to one of the two input terminals of the comparators 31 from the reference power supply 40 so that a reflection signal which is output from a vertically moving color sensor 19 and is supplied to the other input terminal of the comparator 31 through a reflection signal line 16 and a buffer amplifier 30 is compared with the specified reference signal from the reference power supply 40 instead of the reference signal from the reference color sensor 27 of FIG. 4 or 7. Other portions of the operation are identical with those of the arrangement of FIG. 4.

In either of the above embodiments, while moving along the viewing window, color sensor 19 outputs a reflection signal which is compared with the reference signal. The result of the comparison is represented by "1" or "0" as a color difference signal which is then sampled in accordance with the position signals from reed switches sensing the position of the color sensor. Each sample represents the corrected luminosity of the color of resin materials at one of the positions along the viewing window. Samples of the color difference signal are distributed to memories to be stored therein. Depending upon the luminosity of the color difference signal at each position of the resin materials, the indicator lamps 34a through 34m are turned on or off, this permitting the operator to observe the color distribution of resins along the viewing window in the column at a remote location. From the indications of the lamps, the operator may judge how far the separation process has gone or whether the separation is completed. However, it is desirable to release the operator from such judgments.

Another embodiment of the improvement in the arrangement employs an operation processing means for automatically judging the completion of the separation of the two kinds of resin in the treating column on the basis of the samples of the color difference signal and then outputs a separation completion signal is illustrated by the following description with reference to FIGS. 9 through 12.

FIG. 9 is a block diagram showing the arrangement of an operation processing means following the above-mentioned memories 33a through 33m.

Shown at 41 is an input scanner which has input terminals connected respectively to the memories 33a through 33m which form a color difference signal storing means. Shown at 42 is a microprocessor which has an input port 42a connected to the output terminal of the input scanner 41 and an output port 42b connected to control signal lines 43 and 44.

Moreover, an output port 42c is connected to the address signal terminal of the input scanner 41 and input ports 42d and 42e are connected to the output terminal of a stable inversion frequency setting device 45 and a normal separating boundary range setting device 45 respectively. Shown at 47 is a reset signal line which extends from a motor control signal generating circuit 35 to the reset terminal of the microprocessor.

FIG. 10 shows a pattern of the color difference signal stored in the memories 33a through 33m with respect to the status inversion frequency and the status inversion position, i.e. the color distribution of the resins along the viewing window. The pattern illustrated is inherent to the completion of the separation process.

In FIG. 10, the axis of ordinates indicates the status of the color difference signal, i.e. "1" (bright) or "0" (dark) and the axis of abscissas the color difference detection position determined by the position of the reed switches 25a through 25m.

FIGS. 11 (including 11A, 11B and 11C) and 12 (including FIGS. 12A, 12B, 12C and 12D) are flow charts of the microprocessor 42 of FIG. 9.

In operation, as color difference signals are stored in the memories 33a through 33m, the microprocessor 42 starts to operate in response to a reset signal supplied from the motor control signal generating circuit 35 through the reset signal line 47. Digital codes representing the set value regarding the stable inversion frequency and the normal separating boundary range have previously been supplied to and stored in the microprocessor 42. These setting devices 45 and 46 are adapted to produce digital codes representing the set values by proper manual operation. Here, the stable inversion frequency is defined by the frequency or number of the inversions of the status of the color difference signal along the color difference detection positions, which inversion is predicted to occur near the separation boundary when the separation boundary is settled after the completion of the separation of the kinds of the resin.

The inversion frequency of the pattern of FIG. 10 is 1 since there is only one status inversion of the color difference signal at the position between f and g as shown by an arrow. This is an example of the patterns which are judged to indicate that the separation boundary is settled or stabilized when the stable inversion frequency is set to be 1.

The normal separation boundary range is defined by the range of the color difference detection positions within which the separation boundary is empirically predicted to occur when the separation process has normally been carried out and the status inversion is settled, and extends between an upper limit and a lower limit along the viewing window.

In the example of FIG. 10, the upper limit of the normal range of the separation is set at position e and the lower limit is set at position j.

The operation of microprocessor 42 to judge the pattern of FIG. 10 inherent to the completion of the separation process is illustrated by the following description with reference to the flow charts of FIGS. 11 and 12.

Microprocessor 42 starts to operate as shown at the step a in FIG. 11A upon reception of a reset signal. The operation advances to the step b where a second register R2, a third register R3, a fourth register R4 and a fifth register R5 in the microprocessor 42 are cleared. The operation then moves to the step c where the first address of the scanner 41, i.e. the address corresponding to the first memory 33a is set as the initial value in the index register IX in the microprocessor 42.

Subsequently, the operation moves to the step d where the first address of the scanner 41 is designated by the content of the index register IX to read the state of the memory 33a into an accumulator AC. The operation then moves to the step e where the content of the accumulator is stored in the first register R1 in the microprocessor 42.

Subsequently, the operation moves to the step f (FIG. 11B) where 1 is added to the content of the index register. The operation then moves to the step g where the state of the second memory 33b is read into the accumulator AC as described in the step d.

Subsequently, the operation moves to the step h where the comparison between the content of the accumulator, i.e. the state of the second memory 33b and the content of the first register, i.e. the state of the first memory 33a is performed to check or judge the coincidence of the two contents. By this check, whether a status inversion of the color difference signal has occurred between the two adjoining color difference detection positions is determined. If the check results in affirmative, (i.e. if the inversion occurs) the operation moves to the step i where the content ("1" or "0") of the fifth register R5 is judged to see whether it is "1" or not. Since the fifth register R5 has been cleared in the step b, the result of the first judgment is always negative. Thus, the operation moves to the step j where the fifth register is set at "1" state.

Subsequently, the operation moves to the step k where the then existing content of the index register IX which is, in this case, the address corresponding to the second memory 33b is stored in the second register R2.

Thus, the second register R2 stores an address representing a color difference detection position at which a status inversion has occurred and which position is nearest to the first color difference detection position a. This nearest position will be referred to as "uppermost status inversion position".

Subsequently, the operation moves to the step l (FIG. 11C) where the content of the index register IX is stored in the third register R3. As will be described later, the third register R3 is adapted to store an address representing the farthest color difference detection position (hereinafter referred to as "the lowermost status reversion position") from the first color difference detection position in all the color difference detection positions at which inversions occur. However, the content of the third register R3 at the first pass is identical with that of the second register R2.

Subsequently, the operation moves to the step m where 1 is added to the content of the fourth register R4. Here, the frequency of "mismatches" in the result of the judgment at the step h, i.e. the status inversion frequency is stored in the fourth register R4.

Subsequently, the operation moves to the step n where the then existing content of the accumulator AC which is, in this case, the state of the memory 33b is newly stored in the first register R1 to replace the state of the memory 33a which has already been stored therein.

Subsequently, the operation shifts to the step o where a judgment is performed to see whether the content of the index register IX arrived at the final address, i.e. the address corresponding to the final memory 33m or not. When the result of the judgment is negative, the operation returns to the step f. Thereafter the above process, i.e. the renewal of the storage of the lowermost status inversion position and the status inversion frequency are repeated for all the memories 33a through 33m.

Since "1" is stored in the fifth register R5 at the first pass, the result of the judgment at the step i is always affirmative at the second pass or thereafter so that the operation skips over the steps j and k to the step l.

Thus, the address representing the lowermost status inversion position is renewed or updated every time the result of the comparison at the step h is "mismatch", i.e. every time the status inversion occurs, while the address representing the uppermost status inversion position stored in the second register is not renewed until the processor completes all the operation processings and restarts.

When the result of the judgment at the step h is "match", i.e. no status inversion is confirmed, the operation skips over the steps i through m to the step n so that neither the lowermost status inversion position stored in third register nor the status inversion frequency stored in fourth register is renewed or updated.

When these processings are completed for all the memories 33a through 33m the result of the judgment at the step o is affirmative with the address representing the uppermost status inversion position and the lowermost status inversion position being stored in the second register R2 and the third register R3 respectively and the status inversion frequency being stored in the fourth register R4. Subsequently, the operation shifts to the flow chart of FIG. 12 where the pattern of FIG. 10 inherent to the completion of the separation process is judged according to the content of the second, third and fourth registers.

In the operation at step a of FIG. 12A, the content of the fourth register R4 is judged to see whether or not it is 1 or more so that the judgment of the presence of absence of status inversions is made. When any status inversion is confirmed, the result of the judgment is YES.

Subsequently, the operation moves to the step b where the least significant bit of the content of the fourth binary register is judged to see whether it is 1 or not so that the status inversion frequency is judged to see whether it is odd or even. When the status inversion frequency is odd, the operation moves to the step c.

FIG. 10 shows an example of the pattern in which the status inversion frequency is odd (1). The state of the color difference signal is inverted at the position g following the position f. The state of the color difference signal for an upper range from the position a to position f is "1". On the other hand, the state of the color difference signal for a lower range from the position g to the position m is "0". Thus, the pattern represents that the state of the color difference signal at the upper end of the viewing window is different from the state of the color difference signal at the lower end of the viewing window. Whenever the status inversion frequency is odd, regardless of whether it is 1 or not, it is understood that the state of the color difference signal is inverted from the upper end to the lower end of the viewing window 4. Thus, such a pattern represents that the separation process has advanced.

When the color difference signal status inversion frequency is odd as exemplified by the pattern in FIG. 10, the steps c through f in FIG. 12 (FIG. 12B includes steps e to c) are performed to judge whether all the status inversion positions are within a predetermined normal separating boundary range.

Specifically, the content of the second register R2, i.e. the address representing the uppermost status inversion position (e.g. position g in FIG. 10) is judged at the step c to see whether or not it is greater than the set value representing the upper limit level (e.g. position e in FIG. 10) of the normal separating boundary range which has been predetermined by the separating boundary range setting device 46 and stored in the sixth register R6. If the result of the judgment is affirmative, the operation moves to the step d where the content of the second register R2 is judged to see whether or not it is smaller than the numerical value representing the lower limit level (e.g. position j in FIG. 10) of the separating boundary range which has been predetermined by the normal separation boundary range setting device 46 and stored in the seventh register R7. When the result of the judgment is YES, the operation moves to the step e and f where the content of the third register R3, i.e. the address representing the lowermost status inversion position (e.g. position g in FIG. 10) is judged to see whether or not it is greater than the numerical value representing the upper limit level of a separation boundary range which has been determined by the normal separation boundary range setting device 46 and stored in the sixth register R6 and whether or not it is smaller than the numerical value representing the lower limit level of a separation boundary range which has been predetermined by the separation boundary range setting device 46 and stored in the seventh register R7, respectively. When both of the results of the judgment at steps e and f are affirmative the operation moves to the step g.

Whenever the status inversion position g is present between the upper limit level e and the lower limit level j of the separation boundary range as shown by the example in FIG. 10, the results of the judgment at the steps c through f are all affirmative.

Subsequently, the content of the fourth register R4, i.e. the status inversion frequency is judged at the step g to see whether or not it is equal to or smaller than a stable inversion frequency which has been predetermined by the stable inversion frequency setting device 45 and stored in the eighth register R8.

The stable reversion frequency is a measure of the progress of the separation process and varies with the kind of resin, the operating condition of apparatus, etc. Preferably, this factor is empirically determined.

Assuming that the stable inversion frequency has been set at three, the result of the judgment at the step g is YES if the pattern in FIG. 10 is applied. The operation then moves to the step h where a separation completion signal is given to the control signal line 44. Thereafter, the operation stops at the step i.

When any one of the results of the judgment at the steps a through g is negative on the other hand, the operation skips over the step h to the step i and stops here so that no separation completion signals are output.

Thus, as a result of the operation processing following the flow chart, the microprocessor 42 confirms that the pattern of FIG. 10 is inherent to the separation completion and provides a control signal, i.e. a separation completion signal which may be used as a step advancement signal for the subsequent step to the control signal line 44 through the output port 42b.

The above embodiment of the operation processing means is directed to an arrangement in which a plurality of patterns each inherent to one of several stages or phases of the separation process are judged to produce a plurality of control signals so that more precise automatic control is provided is illustrated by the following description with reference to FIGS. 9, 11, 13 and 14.

Figure 13A:
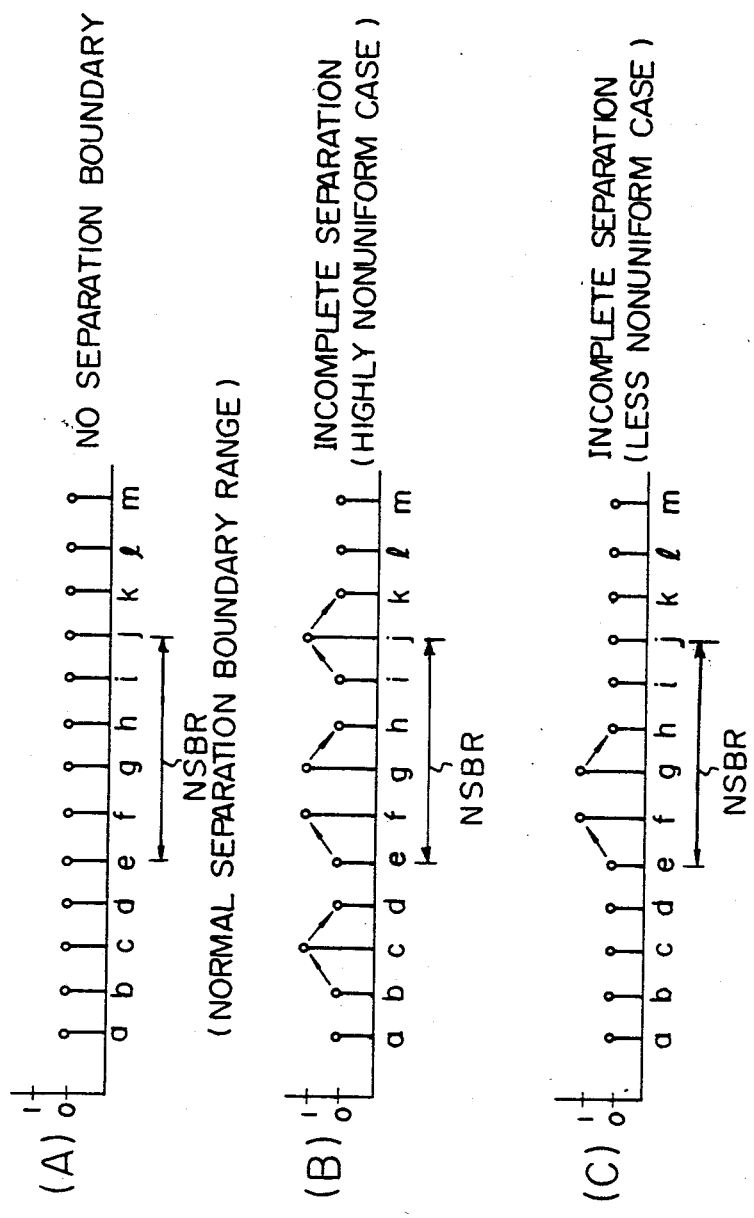
FIG. 13 (including FIGS. 13A and 13B) is a view similar to FIG. 10 regarding a color difference signal applied to still another embodiment of this invention.
Figure 13B:
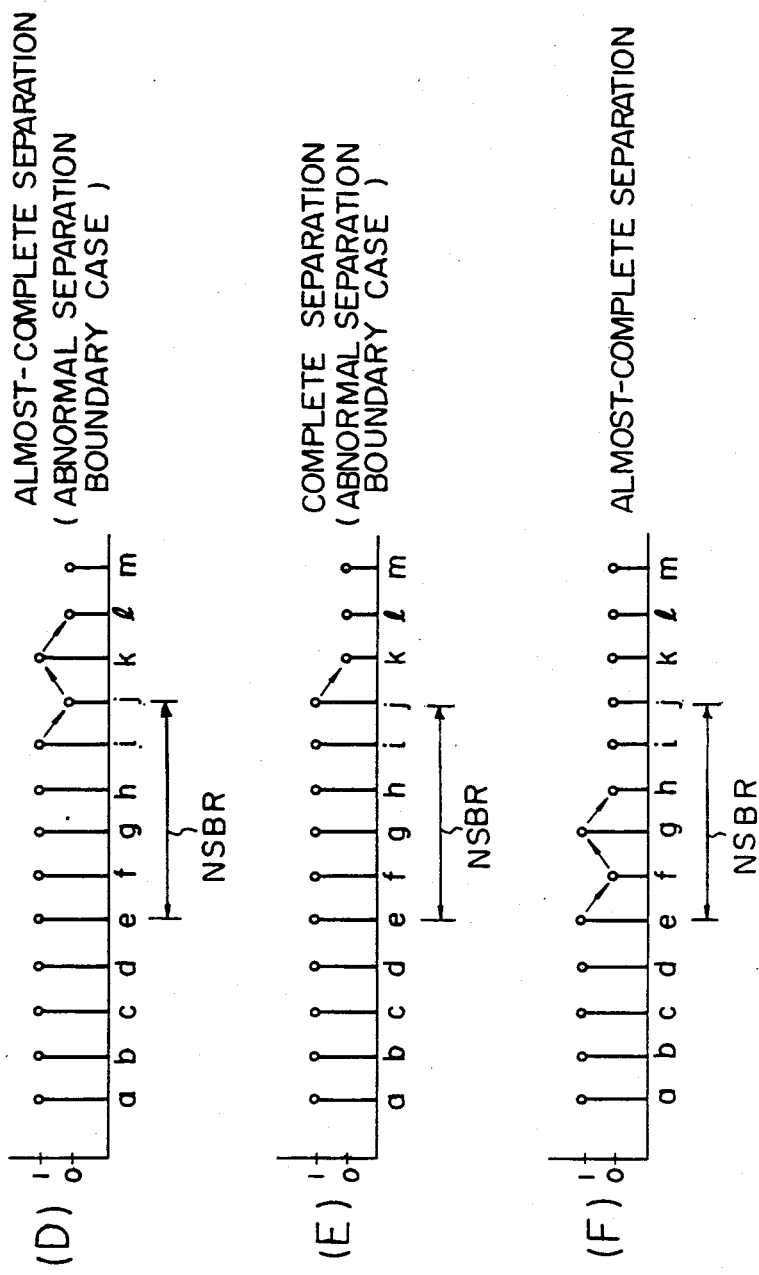

FIG. 13 (including FIGS. 13A and 13B) is a view similar to FIG. 10 showing other patterns of color difference signals stored in the memories 33a through 33m which form color difference signal storing means.

Figure 14A:
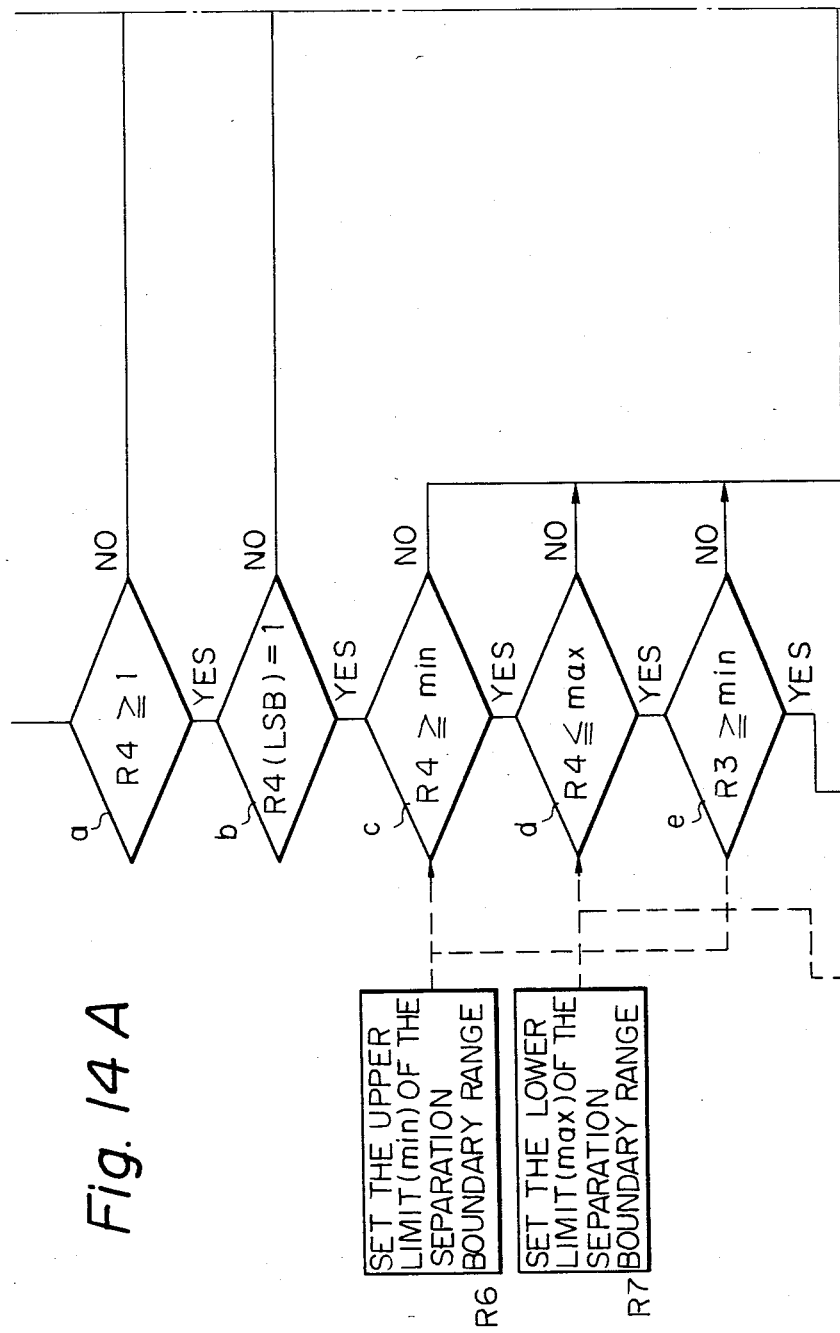
FIG. 14 (including FIGS. 14A, 14B, 14C and 14D) is a partial flow chart similar to FIG. 12 for judging the status inversion frequency and the status inversion position of the color difference signal shown in FIG. 13.

FIG. 14 (including FIGS. 14A, 14B, 14C and 14D) is a flow chart of the microprocessor 42 in FIG. 9. The points indicated by arrows A through F are the results of the judgment when the corresponding patterns (A) through (F) in FIG. 13 are applied [FIG. 13A includes patterns (a) through (C) and FIG. 13B includes patterns (D) through (F)].

Moreover, the control signal buus 43 of FIG. 9 comprises lines 43A through 43F which are allocated to the respective patterns (A) through (F) in FIGS. 13A and 13B. when any one of the patterns (A) through (F) is alternatively confirmed, a control signal corresponding to that pattern is output through the corresponding control signal line.

Figure 11C:
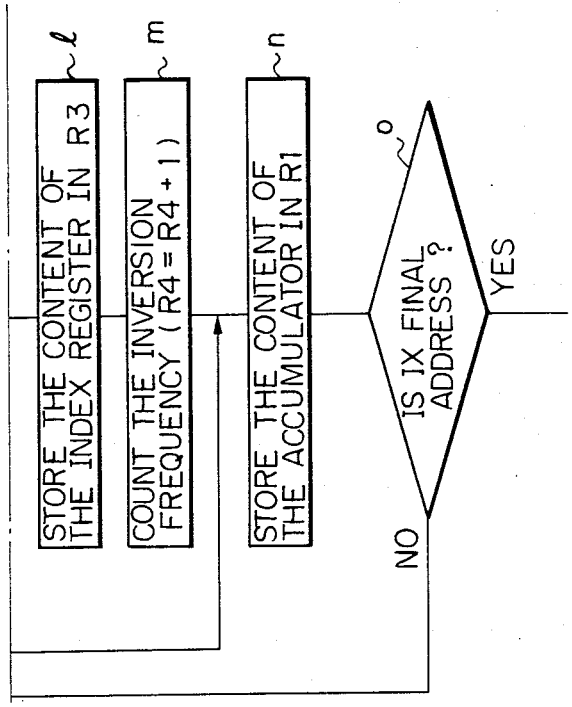
FIG. 11 (including FIGS. 11A, 11B and 11C) is a partial flow chart showing part of the operation processing in the microprocessor shown in FIG. 9.

In the improved embodiment, the microprocessor 42 initially performs the operation processing shown by the flow chart in FIG. 11 (including FIGS. 11A, 11B and 11C) i.e. reads the samples of the color difference signal stored in the memories 33a through 33m, derives the uppermost and lowermost status inversion positions and the status inversion frequency and stores them. Thereafter, the operation moves to the step a in FIG. 14A where the presence or absence of status inversion is judged as in step a of FIG. 12A. When the absence of status inversions is confirmed, the pattern is judged to be a pattern such as the pattern (A) in FIG. 13A representing the absence of separating boundary. Subsequently, the operation moves to the step j where a control signal indicating no separation boundary is output through the control signal line 43A. Thereafter, the operation stops at the step i.

When the presence of status inversions is confirmed at step a of FIG. 14A, the operation shifts to the step b where the status inversion frequency is judged as in the step b of FIG. 12 to check whether it is odd or even. When the status inversion frequency is judged to be even, the operation moves to the step k where the status inversion frequency is judged to see whether or not it is equal to or smaller than a stable inversion frequency which has been predetermined and stored in the eighth register R8. In the following, it is assumed that the stable inversion frequency has been set at three when applied to decision steps k, n, and g. When the result of the judgment is negative, it means that the pattern is inherent to the incomplete separation and highly nonuniform case as exemplified by the pattern (B) in FIG. 13A. Thereafter, the operation moves to the step l in FIG. 14D where a control signal indicating the incomplete separation and highly uniform case is output through the control signal line 43B. Thereafter, the operation stops at the step i in FIG. 14.

When the result of the judgment at the step k in FIG. 14D is YES, the pattern is judged to be inherent in the incomplete separation and less uniform case as exemplified by the pattern (C) in FIG. 13A. Thereafter, the operation moves to the step m in FIG. 14D where a control signal indicating the incomplete separation and less uniform case is output through the control signal line 43c. Thereafter, the operation moves to the step i (STOP) in FIG. 14C.

In the pattern (C) in FIG. 13A, the status inversion is present by chance within the normal separating boundary range. However it is noted that the step k does not judge whether the inversion is within the separation boundary range.

When the result of the judgment at the step b of FIG. 14 is that the inversion frequency is an odd number, the operation moves to the steps c through f in FIG. 14A where the uppermost and lowermost status inversion positions are judged as in the steps c through f in FIG. 12 (FIG. 12A includes steps a through d and FIG. 12B includes steps e through i) to see whether or not they are present between the upper limit level and the lower limit level of a predetermined normal separation boundary range, i.e. whether or not all the status inversion positions are present within the normal separating boundary range.

When the result of the judgment at the steps c through f is negative, the operation moves to the step n in FIG. 14C where the status inversion frequency is judged to determine whether it is equal to or smaller than the stable inversion frequency or not.

When the result of the judgment at the step n is negative, the pattern such as the pattern (D) of FIG. 13B is judged to be inherent in the almost complete separation and abnormal separating boundary case. Thereafter, the operation moves to the step o in FIG. 14D where a control signal indicating the almost complete separation and abnormal separating boundary case is output through the control signal line 43D. Thereafter, the operation stops at the step i (STOP) of FIG. 14C.

When the result of the judgment at the step n in FIG. 14C is affirmative the patter is judged to be inherent in the complete separation and abnormal separation boundary case shown by the pattern (E) in FIG. 13B. Thereafter, the operation moves to the step p in FIG. 14C where a control signal indicating the complete separation and abnormal separation boundary case is output through the control signal line 43E. Thereafter, the operation stops at the step i in FIG. 14C.

When the result of the judgment at the steps c through f in FIG. 14 (FIG. 14A includes steps a through e and FIG. 14C includes steps f-i, p, q and n) are all affirmative, i.e. all the status inversion positions are present within the normal separating boundary range, the operation moves to the step g in FIG. 14C where the status inversion frequency is judged as in the step g in FIG. 12B to determine whether it is equal to or smaller than the stable inversion frequency.

When the result of the judgment at the step g of FIG. 14C is negative, the pattern is judged to be inherent in the almost complete separation as exemplified by the pattern (F) in FIG. 13B. Thereafter, the operation moves to the step q in FIG. 14C where a control signal indicating the almost complete separation is output through the control signal line 43F. Thereafter, the operation stops at the step i in FIG. 14C.

When the result of the judgment at the step g of FIG. 14C is affirmative, the pattern is judged to be inherent in the complete separation as exemplified by the pattern in FIG. 10. Thereafter, the operation shifts to the step h in FIG. 14C where a separation completion signal is output as in the step h in FIG. 12B. Thus, the same operation as the embodiment according to the flow chart in FIG. 12 is assured. By this operation processing following the flow chart, microprocessor 42 judges each of the patterns of FIG. 13 to select and supply one of a plurality of control signals corresponding to the separation condition of the resin to the subsequent step from the output port 42b through the control signal lines 43A through 43F.

In the above operation processing, the processing steps are performed one by one while reading a 1-bit color different signal stored in the memories 33a through 33m in order. When the processing is performed with the final color difference signal the uppermost and lowermost status inversion positions and the status inversion frequency which are necessary for the pattern judgment are stored. Thus, the load on the microprocessor 42 is extremely light.

The above flow chart includes three steps for the judgment of the stable inversion frequency. The flow chart may optionally be arranged so that a separate stable inversion frequency can be predetermined for each step by the stable inversion frequency setting device 45.

Referring again to the color sensor 19, the light-projecting section 11 is provided with the light-projecting lens 10 and the light-receiving station 17 with the light-receiving lens 13. Since the purpose of both the light-projecting section 11 and the light-receiving section 17 can be attained at least when the reflection of the light emitted by the light-projecting section 11 reaches the light-receiving section 17, the arrangement may optionally be free of the light-projecting lens 11 and the light-receiving lens 17 if enough light is obtained from the light source.

Although the light-receiving section 17 is provided with the visibility filter 14, the arrangement may optionally be such that the filter is mounted on the light-projecting section 11 instead of the light-receiving section 17 since the purpose of the filter 14 is attained at least when the desired wave length v.s. transmissivity characteristic for the entire light path from the light-projecting section 11 to the light-receiving section 17 is obtained.

Referring again to the light-receiving section 17, as an example of the filter there may be employed a visibility lens simulating the visibility of the naked eye. However, the characteristics of the filter 14 are not limited to such visibility, and suitable filters having an optimum wave length v.s. transmissivity characteristic for the recognition of the color difference inherent in substances such as resins are preferred.

Moreover, the arrangement of the light-receiving section 17 may optionally be free of a filter if a photoelectric transducer designed to singly provide a positive differentiation of the slight color difference between materials to be monitored is employed as the photoelectric transducer 15.

The position sensing means as exemplified in the embodiment comprises reed switches having a plurality of physical positions in the path of the movable color sensor and a magnet carried by the color sensor for successively and alternately activating the reed switches.

Referring again to the microprocessor 42, the operation for the judgment of the separation completion pattern as a stage of the separation process is performed as illustrated in the description. However, the above operation is attained at least when the pattern inherent in the separation completion is finally confirmed by judging status inversions having odd numbers of frequency equal to or less than the stable inversion frequency within the normal separating boundary range. Therefore, there is no doubt that the separation completion with reference to this invention includes color difference signal patterns formed by a substance-space boundary, e.g. the charged level of the substance in the treating column.

I claim:

1. An apparatus for monitoring the interior of a treating column containing two types of materials, said apparatus comprising:
   a viewing window provided on a side wall of the column;
   a color sensor having a light projecting portion placed to face the window for projecting light to materials in an area within the column to be monitored through the viewing window and a light reception portion for receiving a light reflected from the materials and converting the light to a reflection signal corresponding to the color of the materials;
   driving means for driving the color sensor to move along the viewing window whereby the movement of the color sensor produces a scanned reflection signal indicating the color profile of the materials;
   position sensing means for successively producing position signals each indicating the passing of the color sensor by one of a plurality of predetermined color detection positions spaced along the viewing window as the color sensor is moved by the driving means;
   reference means for providing a reference signal for differentiation of the colors of the two types of materials contained in the column;
   means for comparing the scanned reflection signal from the moving color sensor with the reference signal from the reference means to produce a color difference signal for identification of the type of the materials; and
   means for position-defining the color difference signal in accordance with the successively sensed position signals from the position sensing means to develop a series of color difference samples each identifying the type of materials dominantly present at one of the successive detection areas within the column and spaced generally in the vertical axis thereof, whereby said series of samples indicates the distribution of the materials over the vertically scanned areas within the column.

2. An apparatus according to claim 1 further comprising:
   operation processing means for processing said series of said color difference samples and for producing a signal indicating the completion of separation process when said series of said samples is recognized to have a preselected pattern.

3. An apparatus according to claim 1 wherein said materials contained in said column having radioactivity so that it is hazardous for a human to have an access to said column, said apparatus further comprising: a light source located at a remote place from said column, and optical fiber means for transmitting the light from said source to said color sensor located at said column, whereby the maintenance of said light source can be made in a safety environment, while permitting the size of said color sensor to be relatively compact.

4. An apparatus for monitoring the interior of a treating column containing two types of materials, said apparatus comprising:
- a viewing window provided on a side wall of the column;
- a color sensor having alight projecting portion placed to face the window for projecting light to materials in an area within the column to be monitored through the viewing window and a light reception portion for receiving a light reflected from the materials and converting the light to a reflection signal corresponding to the color of the materials;
- driving means for driving the color sensor to move along the viewing window whereby the movement of the color sensor produces a scanned reflection signal indicating the color profile of the materials;
- position sensing means for successively producing position signals each indicating the passing of the color sensor by one of a plurality of predetermined color detection positions spaced along the viewing window as the color sensor is moved by the driving means;
- a reference color sensor having a light projecting means placed to face material in the treating column at a reference position thereof for projection light to the material and a light reception portion for receiving light from the material at the reference position and converting the light to a reference signal corresponding to the color of the material at the reference position whereby the reference signal compensates for variations in the color characteristics of the materials in the column as caused by aging;
- means for comparing the scanned reflection signal from the moving color sensor with the reference signal to produce a color difference signal for identification of the type of the materials;
- means for position-defining the color difference signal in accordance with the successively sensed position signals from the position sensing means to develop a series of color difference samples each identifying the type of the materials dominantly present at one of the successive detection areas within the column and spaced generally in the vertical axis thereof, whereby said series of samples indicates the distribution of the materials over the vertically scanned areas within the column; and
- memory means coupled with the position defining means for storing said series of samples.

5. An apparatus according to claim 4 further comprising:
- operation processing means coupled with said memory means for processing said series of said color difference samples and for producing a signal indicating the completion of separation process when said series of said samples is recognized to have a preselected pattern.

6. An apparatus according to claim 4 wherein said materials contained in said column have radioactivity so that it is hazardous for a human to have an access to said column, said apparatus further comprising: at least one light source located at a remote place from said column, and optical fiber means for transmitting the light from said source to said color sensor and said reference color sensor located at said column, whereby the maintenance of said light source can be made in a safety environment, while permitting the size of said color sensor and said reference color sensor to be relatively compact.

7. An apparatus for monitoring the interior of a treating column containing two types of materials, said apparatus comprising:
- a viewing window provided on a side wall of the column;
- a color sensor having a light projecting portion placed to face the window for projecting light to materials in an area within the column to be monitored through the viewing window and a light reception portion for receiving a light reflected from the materials and converting the light to a reflection signal corresponding to the color of the materials;
- driving means for driving the color sensor to move along the viewing window whereby the movement of the color sensor produces a scanned reflection signal indicating the color profile of the materials
- position sensing means for successively producing position signals each indicating the passing of the color sensor by one of a plurality of predetermined color detection positions spaced along the viewing window as the color sensor is moved by the driving means;
- reference means including reference position sensing means for producing a reference position signal indicating the passing of the moving color sensor by a predetermined reference position on the viewing window, and reference signal storage means responsive to the reference position signal for storing, as a reference signal, a reflection signal from the color sensor which signal indicates the color of the material present at a reference area within the column whereby the reference means not only compensates for variations in the color characteristics of the materials in the column as caused by aging but also obviates an additional color sensor dedicated to the provision of the reference signal and having a similar structure to said movable color sensor;
- means for comparing the scanned reflection signal from the moving color sensor with the reference signal to produce a color difference signal for identification of the type of the materials;
- means for position-defining the color difference signal in accordance with the successively sensed position signals from the position sensing means to develop a series of color difference samples each identifying the type of the materials dominantly present at one of the successive detection areas within the column and spaced generally in the vertical axis thereof, whereby said series of samples indicates the distribution of the materials over the vertically scanned areas within the column; and
- memory means coupled with the position defining means for storing said series of samples.

8. An apparatus according to claim 7 further comprising:
- operation processing means coupled with said memory means for processing said series of said color difference samples and for producing a signal indicating the completion of separation process when said series of said samples is recognized to have a preselected pattern.

9. An apparatus according to claim 7 wherein said materials contained in said column have radioactivity so that it is hazardous for a human to have an access to said column, said apparatus further comprising: a light source located at a remote place from said column, and optical fiber means from transmitting the light from said source to said color sensor located at said column whereby the maintenance of said light source can be made in a safety environment, while permitting the size of said color sensor to be relatively compact.

10. An apparatus for monitoring the interior of a treating column comprising:
  a viewing window provided on a side wall of the column;
  a color sensor having a light projecting portion placed to face the window for projecting light to materials in the column to be monitored through the viewing windiw and a light reception portion for receiving a light reflected from the materials and converting the light to a reflection signal corresponding to the color of the materials;
  driving means for driving the color sensor to move along the viewing window;
  position sensing means for producing position signals each indicating the presence of the color sensor at one of a plurality of color detection positions spaced along the viewing window;
  a reference color sensor having a light projecting means placed to face material in the treating column at a reference position thereof for projecting light to the material and a light reception portion for receiving light from the material at the reference position and converting the light to a reference signal corresponding to the color of the material at the reference position;
  a comparator for comparing the reflection signal from the color sensor with the reference signal from the reference color sensor to produce a color difference signal;
  a plurality of memory elements;
  circuit means for distributing the color difference signal to one of said memories in accordance with the position signals from the position sensing means; and
  operation processing means for processing the color difference signal from the plurality of the memory elements and for producing a signal indicating the completion of separation process when the inversion frequency of the color difference signal from the memory elements is an odd number equal to or less than a predetermined stable inversion frequency and all the inversion positions of the color difference signal are within a predetermined range of a normal separation boundary.

11. An apparatus for monitoring the interior of a treating column comprising:
  a viewing window provided on a side wall of the column;
  a color sensor having a light projecting portion placed to face the window for projecting light to materials in the column to be monitored through the viewing window and a light reception portion for receiving a light reflected from the materials and converting the light to a reflection signal corresponding to the color of the materials;
  driving means for driving the color sensor to move along the viewing window;
  position sensing means for producing position signals each indicating the presence of the color sensor at one of a plurality of color detection positions spaced along the viewing window;
  reference position sensing means for producing a reference position signal indicating the presence of the color sensor at a reference position on the viewing window;
  reference signal storage means responsive to the reference position signal for storing, as a reference signal, a reflection signal from the color sensor;
  a comparator for comparing the reflection signal from the color sensor with the reference signal from the reference signal storage means to produce a color difference signal;
  a plurality of memory elements;
  circuit means for distributing the color difference signal to one of said memories in accordance with the position signals from the position sensing means; and
  operation processing means for processing the color difference signal from the plurality of the memory elements and for producing a signal indicating the completion of separation process when the inversion frequency of the color difference signal from the memory elements is an odd number equal to or less than a predetermined stable inversion frequency and all the inversion positions of the color difference signal are within a predetermined range of a normal separation boundary.

12. An apparatus for monitoring the interior of a treating column comprising:
  a viewing window provided on a side wall of the column;
  a color sensor having a light projecting portion placed to face the window for projecting light to materials in the column to be monitored through the viewing window and a light reception portion for receiving a light reflected from the materials and converting the light to a reflection signal corresponding to the color of the materials;
  driving means for driving the color sensor to move along the viewing window;
  position sensing means for producing position signals each indicating the presence of the color sensor at one of a plurality of color detection positions spaced along the viewing window;
  reference signal generating means for generating a predetermined reference signal;
  a comparator for comparing the reflection signal from the color sensor with the reference signal from the reference signal generating means to produce a color difference signal;
  a plurality of memory elements;
  circuit means for distributing the color difference signal to one of said memories in accordance with the position signals from the position sensing means; and
  operation processing means for processing the color difference signal from the plurality of the memory elements and for producing a signal indicating the completion of separation process when the inversion frequency of the color difference signal from the memory elements is an odd number equal to or less than a predetermined stable inversion frequency and all the inversion positions of the color difference signal are within a predetermined range of a normal separation boundary.

13. An apparatus for monitoring the interior of a treating column comprising:
  a viewing window provided on a side wall of the column;

a color sensor having a light projecting portion placed to face the window for projecting light to materials in the column to be monitored through the viewing window and a light reception portion for receiving a light reflected from the materials and converting the light to a reflection signal corresponding to the color of the materials;

driving means for driving the color sensor to move along the viewing window;

position sensing means for producing position signals each indicating the presence of the color sensor at one of a plurality of color detection positions spaced along the viewing window;

a reference color sensor having a light projecting means placed to face material in the treating column at a reference position thereof for projecting light to the material and a light reception portion for receiving light from the material at the reference position and converting the light to a reference signal corresponding to the color of the material at the reference position;

a comparator for comparing the reflection signal from the color sensor with the reference signal from the reference color sensor to produce a color difference signal;

a plurality of memory elements;

circuit means for distributing the color difference signal to one of said memories in accordance with the position signals from the position sensing means; and operation processing means for processing the color difference signal from the plurality of the memory elements and for recognizing no separation boundary when the inversion frequency of the color difference signal from the memory elements is equal to zero, the state of incomplete separation when the inversion frequency of the color difference signal is an even number, the state of abnormal separation boundary when the inversion frequency is an odd number but at least one of the inversion positions is out of a predetermined normal range of separation boundary, the state of almost complete separation when the inversion positions are all within the predetermined normal range of separation boundary and the inversion frequency is an odd number but is greater than the number of a predetermined stable inversion frequency, the state of complete separation when the inversion positions are all within the predetermined normal range of separation boundary and the inversion frequency is an odd number at most equal to the number of the stable inversion frequency whereby one of a plurality control signals each indicating one of said recognzied states is selectively produced in accordance with the condition of materials in the treating column.

14. An apparatus for monitoring the interior of a treating column comprising:

a viewing window provided on a side wall of the column;

a color sensor having a light projecting portion placed to face the window for projecting light to materials in the column to be monitored through the viewing window and a light reception portion for receiving a light reflected from the materials and converting the light to a reflection signal corresponding to the color of the materials;

driving means for driving the color sensor to move along the viewing window;

position sensing means for producing position signals each indicating the presence of the color sensor at one of a plurality of color detection positions spaced along the viewing window;

reference position sensing means for producing a reference position signal indicating the presence of the color sensor at a reference position on the viewing window;

reference signal storage means responsive to the reference position signal for storing, as a reference signal, a reflection signal from the color sensor;

a comparator for comparing the reflection signal from the color sensor with the reference signal from the reference signal storage means to produce a color difference signal;

a plurality of memory elements;

circuit means for distributing the color difference signal to one of said memories in accordance with the position signals from the position sensing means; and operation processing means for processing the color difference signal from the plurality of the memory elements and for recognizing no separation boundary when the inversion frequency of the color difference signal from the memory elements is equal to zero, the state of incomplete separation when the inversion frequency of the color difference signal is an even number, the state of abnormal separation boundary when the inversion frequency is an odd number but at least one of the inversion positions is out of a predetermined normal range of separation boundary, the state of almost complete separation when the inversion positions are all within the predetermined normal range of separation boundary and the inversion frequency is an odd number but is greater than the number of a predetermined stable inversion frequency, the state of complete separation when the inversion positions are all within the predetermined normal range of separation boundary and the inversion frequency is an odd number at most equal to the number of the stable inversion frequency whereby one of a plurality control signals each indicating one of said recognized states is selectively produced in accordance with the condition of materials in the treating column.

15. An apparatus for monitoring the interior of a treating column comprising:

a viewing window provided on a side wall of the column;

a color sensor having a light projecting portion placed to face the window for projecting light to materials in the column to be monitored through the viewing window and a light reception portion for receiving a light reflected from the materials and converting the light to a reflection signal corresponding to the color of the materials;

driving means for driving the color sensor to move along the viewing window;

position sensing means for producing position signals each indicating the presence of the color sensor at one of a plurality of color detection positions spaced along the viewing window;

reference signal generating means for generating a predetermined reference signal;

a comparator for comparing the reflection signal from the color sensor with the reference signal from the reference signal generating means to produce a color difference signal;

a plurality of memory elements;

circuit means for distributing the color difference signal to one of said memories in accordance with the position signals from the position sensing means; and operation processing means for processing the color difference signal from the plurality of the memory elements and for recognizing no separation boundary when the inversion frequency of the color difference signal from the memory elements is equal to zero, the state of incomplete separation when the inversion frequency of the color difference signal is an even number, the state of abnormal separation boundary when the inversion frequency is an odd number but at least one of the inversion positions is out of a predetermined normal range of separation boundary, the state of almost complete separation when the inversion positions are all within the predetermined normal range of separation boundary and the inversion frequency is an odd number but is greater than the number of a predetermined stable inversion frequency, the state of complete separation when the inversion positions are all within the predetermined normal range of separation boundary and the inversion frequency is an odd number at most equal to the number of the stable inversion frequency whereby one of a plurality control signals each indicating one of said recognized states is selectively produced in accordance with the condition of materials in the treating column.

* * * * *